US012702467B2

(12) United States Patent
Batchelor et al.

(10) Patent No.: US 12,702,467 B2
(45) Date of Patent: Aug. 11, 2026

(54) MULTIPLE MODE ELECTROSURGICAL DEVICE

(71) Applicant: GYRUS ACMI, INC., Westborough, MA (US)

(72) Inventors: Kester Julian Batchelor, Mound, MN (US); Eric G. Tate, Maple Grove, MN (US); Theodore C. Blus, Arden Hills, MN (US); Richard J. Curtis, Corcoran, MN (US); Nikhil M. Murdeshwar, Maple Grove, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 529 days.

(21) Appl. No.: 18/047,316

(22) Filed: Oct. 18, 2022

(65) Prior Publication Data

US 2023/0132239 A1 Apr. 27, 2023

Related U.S. Application Data

(63) Continuation of application No. 15/632,786, filed on Jun. 26, 2017, now Pat. No. 11,510,698.

(Continued)

(51) Int. Cl.

*A61B 18/14* (2006.01)
*A61B 18/12* (2006.01)
*A61B 18/00* (2006.01)

(52) U.S. Cl.

CPC ...... *A61B 18/1233* (2013.01); *A61B 18/1402* (2013.01); *A61B 2018/00607* (2013.01);

(Continued)

(58) Field of Classification Search

CPC ...... A61B 18/1402; A61B 2018/00958; A61B 2018/1253; A61B 2018/1412

See application file for complete search history.

(56) References Cited

U.S. PATENT DOCUMENTS 4,089,336 A 5/1978 Cage et al.
4,202,337 A * 5/1980 Hren .................. A61B 18/1402 606/50

(Continued)

FOREIGN PATENT DOCUMENTS

CN 1610526 A 4/2005
CN 102164556 A 8/2011

(Continued)

OTHER PUBLICATIONS

"U.S. Appl. No. 15/632,786, 312 Amendment filed Oct. 12, 2022", 8 pgs.

(Continued)

*Primary Examiner* — Jaymi E Della
(74) *Attorney, Agent, or Firm* — Schwegman Lundberg & Woessner, P.A.

(57) ABSTRACT

An electrosurgical device having first and second poles; blade electrode with a metal shim having two opposing faces and one or more facets, a nonconductive coating which covers at least the faces and a portion of the facets of the metal shim, while a distal portion of the one or more facets remains uncovered by the nonconductive coating; a lateral electrode comprised of a broad shim having one or more conductive faces and is placed parallel to the blade electrode so that at least one of the one or more conductive faces is exposed and a distal end of the blade electrode protrudes from the lateral electrode; the lateral electrode is fixed stationary relative to the blade electrode; the nonconductive coating insulates the blade electrode from the lateral electrode; and the first pole is connected to the blade electrode and the second pole is connected to the lateral electrode.

18 Claims, 12 Drawing Sheets

Related U.S. Application Data

(60) Provisional application No. 62/358,787, filed on Jul. 6, 2016.

(52) U.S. Cl.
CPC ............... *A61B 2018/00958* (2013.01); *A61B 2018/1253* (2013.01); *A61B 2018/1412* (2013.01)

(56) References Cited

U.S. PATENT DOCUMENTS

| | | | | |
|---|---|---|---|---|
| 4,481,057 | A | 11/1984 | Beard | |
| 5,472,442 | A | 12/1995 | Klicek | |
| 5,562,720 | A | 10/1996 | Stern et al. | |
| 5,752,951 | A | 5/1998 | Yanik | |
| 6,190,383 | B1 | 2/2001 | Schmaltz et al. | |
| 8,177,783 | B2 | 5/2012 | Davison et al. | |
| 8,394,088 | B2 | 3/2013 | West, Jr. | |
| 8,992,520 | B2 | 3/2015 | Van Wyk et al. | |
| 9,168,082 | B2 | 10/2015 | Evans et al. | |
| 2003/0130658 | A1 | 7/2003 | Goble et al. | |
| 2003/0163123 | A1 | 8/2003 | Goble et al. | |
| 2004/0082946 | A1 | 4/2004 | Malis et al. | |
| 2005/0065509 | A1 | 3/2005 | Coldwell et al. | |
| 2005/0283149 | A1 | 12/2005 | Thorne et al. | |
| 2006/0047280 | A1 | 3/2006 | Goble et al. | |
| 2006/0111709 | A1* | 5/2006 | Goble ................ | A61B 18/1402 606/48 |
| 2006/0241587 | A1* | 10/2006 | Heim ................ | A61B 18/1402 606/50 |
| 2007/0265619 | A1 | 11/2007 | Ariola et al. | |
| 2008/0071263 | A1 | 3/2008 | Blaha | |
| 2008/0140066 | A1* | 6/2008 | Davison ............ | A61B 18/1402 606/37 |
| 2008/0287948 | A1* | 11/2008 | Newton ............ | A61B 18/1206 606/50 |
| 2009/0093804 | A1* | 4/2009 | Newton ............ | A61B 18/1206 606/33 |
| 2009/0138013 | A1 | 5/2009 | Thorne et al. | |
| 2009/0234352 | A1 | 9/2009 | Behnke et al. | |
| 2010/0010485 | A1* | 1/2010 | West, Jr. ........... | A61B 18/1482 606/37 |
| 2011/0082494 | A1 | 4/2011 | Kerr et al. | |
| 2013/0023871 | A1* | 1/2013 | Collins ............. | A61B 18/1233 606/34 |
| 2013/0041363 | A1 | 2/2013 | Van Wyk et al. | |
| 2014/0276786 | A1 | 9/2014 | Batchelor | |
| 2014/0276796 | A1 | 9/2014 | Batchelor et al. | |
| 2014/0276800 | A1 | 9/2014 | Batchelor et al. | |
| 2014/0276804 | A1 | 9/2014 | Batchelor | |
| 2015/0119885 | A1 | 4/2015 | Windgassen et al. | |
| 2015/0282873 | A1 | 10/2015 | Batchelor et al. | |
| 2016/0120588 | A1* | 5/2016 | Amoah ............. | A61B 18/1206 606/39 |
| 2018/0008312 | A1 | 1/2018 | Batchelor et al. | |

FOREIGN PATENT DOCUMENTS

| | | | |
|---|---|---|---|
| CN | 102475574 | A | 5/2012 |
| CN | 103800070 | A | 5/2014 |
| CN | 204092175 | U | 1/2015 |
| CN | 107582163 | A | 1/2018 |
| CN | 107582163 | B | 12/2020 |
| EP | 1499242 | A2 | 1/2005 |
| EP | 2047816 | A2 | 4/2009 |
| EP | 2777587 | A1 | 9/2014 |
| EP | 2789305 | A1 | 10/2014 |
| EP | 3266399 | A1 | 1/2018 |
| JP | H09168547 | A | 6/1997 |
| JP | 2005523059 | A | 8/2005 |
| JP | 2008073527 | A | 4/2008 |
| JP | 2011527612 | A | 11/2011 |
| JP | 2018029950 | A | 3/2018 |
| JP | 6537564 | B2 | 6/2019 |
| WO | WO-03088806 | A2 | 10/2003 |

OTHER PUBLICATIONS

"U.S. Appl. No. 15/632,786, Corrected Notice of Allowability mailed Jul. 20, 2022", 3 pgs.
"U.S. Appl. No. 15/632,786, Examiner Interview Summary mailed Mar. 11, 2020", 3 pgs.
"U.S. Appl. No. 15/632,786, Examiner Interview Summary mailed Mar. 21, 2022", 3 pgs.
"U.S. Appl. No. 15/632,786, Examiner Interview Summary mailed Mar. 25, 2021", 2 pgs.
"U.S. Appl. No. 15/632,786, Final Office Action mailed Aug. 31, 2021", 29 pgs.
"U.S. Appl. No. 15/632,786, Final Office Action mailed Dec. 2, 2019", 21 pgs.
"U.S. Appl. No. 15/632,786, Non Final Office Action mailed Apr. 16, 2021", 23 pgs.
"U.S. Appl. No. 15/632,786, Non Final Office Action mailed Jun. 27, 2019", 21 pgs.
"U.S. Appl. No. 15/632,786, Non Final Office Action mailed Oct. 13, 2020", 23 pgs.
"U.S. Appl. No. 15/632,786, Notice of Allowance mailed Jul. 13, 2022", 9 pgs.
"U.S. Appl. No. 15/632,786, PTO Response to Rule 312 Communication mailed Oct. 19, 2022", 2 pgs.
"U.S. Appl. No. 15/632,786, Response filed Mar. 12, 2021 to Non Final Office Action mailed Oct. 13, 2020", 16 pgs.
"U.S. Appl. No. 15/632,786, Response filed Mar. 25, 2019 to Restriction Requirement mailed Feb. 11, 2019", 8 pgs.
"U.S. Appl. No. 15/632,786, Response filed Apr. 2, 2020 to Final Office Action mailed Dec. 2, 2019", 15 pgs.
"U.S. Appl. No. 15/632,786, Response filed Aug. 16, 2021 to Non Final Office Action mailed Apr. 16, 2021", 16 pgs.
"U.S. Appl. No. 15/632,786, Response filed Sep. 27, 2019 to Non Final Office Action mailed Jun. 27, 2019", 20 pgs.
"U.S. Appl. No. 15/632,786, Response filed Dec. 30, 2021 to Final Office Action mailed Aug. 31, 2021", 19 pgs.
"U.S. Appl. No. 15/632,786, Restriction Requirement mailed Feb. 11, 2019", 6 pgs.
"U.S. Appl. No. 15/632,786, Supplemental Amendment Filed Mar. 30, 2022", 9 pgs.
"Chinese Application Serial No. 201710536884.6, Office Action mailed Jun. 15, 2020", w/ English Translation, 24 pgs.
"Chinese Application Serial No. 201710536884.6, Office Action mailed Oct. 28, 2019", with English translation, 20 pgs.
"Chinese Application Serial No. 201710536884.6, Response filed Mar. 11, 2020 to Office Action mailed Oct. 28, 2019", w/ English Claims, 55 pgs.
"Chinese Application Serial No. 201710536884.6, Response filed Aug. 28, 2020 to Office Action mailed Jun. 15, 2020", 7 pgs.
"European Application Serial No. 17178239.4, Response filed Apr. 7, 2022 to Communication Pursuant to Article 94(3) EPC mailed Oct. 7, 2021", 95 pgs.
"European Application Serial No. 17178239.4, Communication Pursuant to Article 94(3) EPC mailed Jan. 2, 2020", 7 pgs.
"European Application Serial No. 17178239.4, Communication Pursuant to Article 94(3) EPC mailed Oct. 7, 2021", 9 pgs.
"European Application Serial No. 17178239.4, Extended European Search Report mailed Dec. 11, 2017", 7 pgs.
"European Application Serial No. 17178239.4, Response filed Apr. 27, 2018 to Extended European Search Report mailed Dec. 11, 2017", 11 pgs.
"European Application Serial No. 17178239.4, Response filed May 2, 2020 to Communication Pursuant to Article 94(3) EPC mailed Jan. 2, 2020", 12 pgs.
"Japanese Application Serial No. 2017-130702, Notice of Reasons for Rejection mailed Jul. 31, 2018", w/ English Translation, 8 pgs.

(56) References Cited

OTHER PUBLICATIONS

"Japanese Application Serial No. 2017-130702, Response filed Jan. 22, 2019 to Notice of Reasons for Rejection mailed Jul. 31, 2018", w/ English Translation, 9 pgs.

* cited by examiner

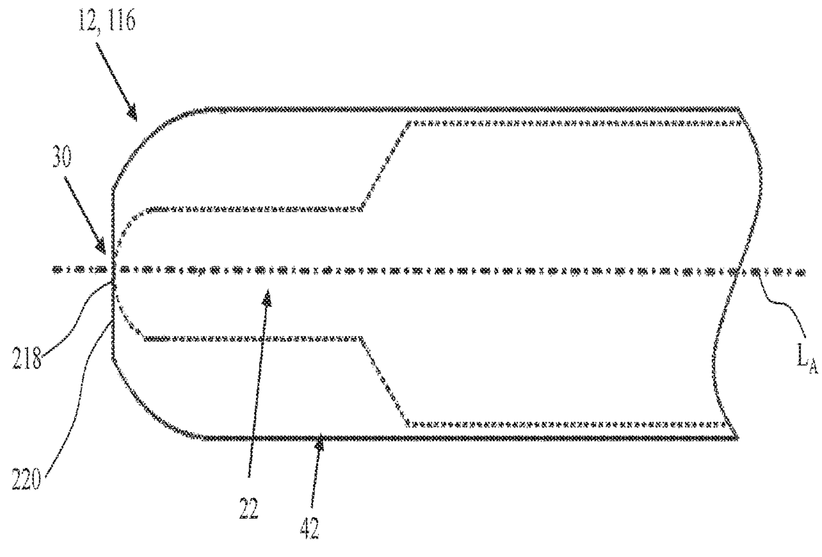
FIG. 11
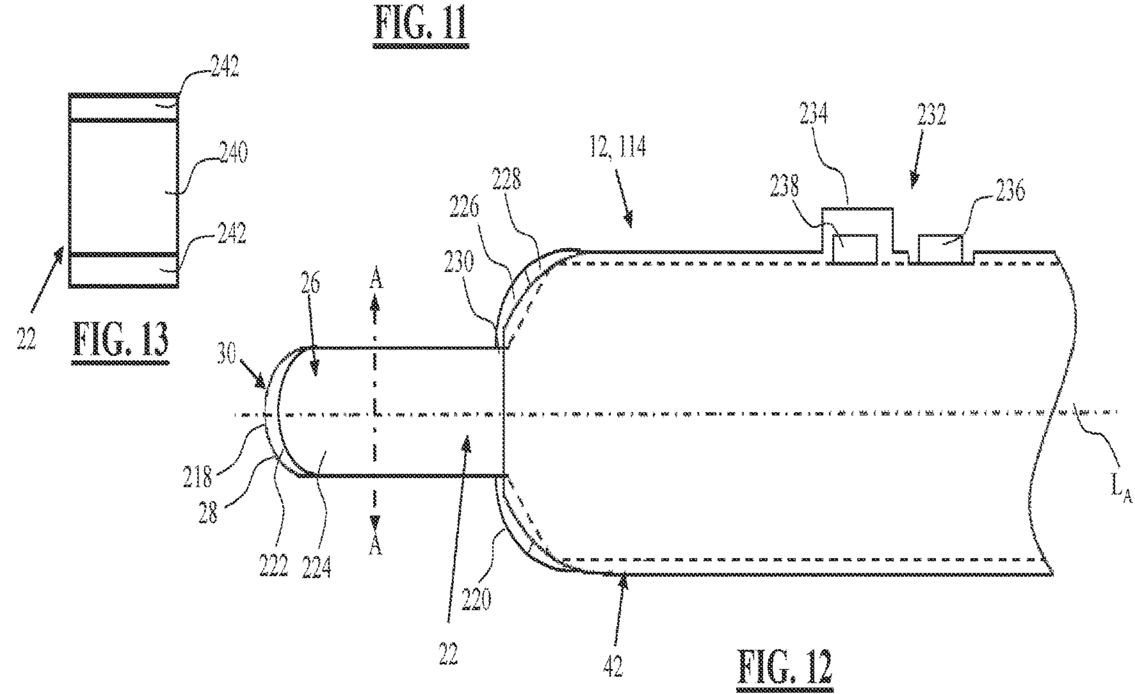
FIG. 13
FIG. 12

54
56b
56a
57

54
56b
56a
57

55
54
56b
55b
56a
55a
57

MULTIPLE MODE ELECTROSURGICAL DEVICE

PRIORITY CLAIM

This application is a Continuation of U.S. patent application Ser. No. 15/632,786, filed Jun. 26, 2017 now U.S. Pat. No. 11,510,698, which claims the benefit of priority to U.S. Provisional Application Ser. No. 62/358,787, filed Jul. 6, 2016, the contents of which are incorporated herein by reference in their entireties.

FIELD

The present teachings generally relate to an electrosurgical blade which is able to operate in two separate monopolar modes. The electrosurgical blade may find particular use in providing a user with a blade for precision cutting in a first monopolar mode, and a blade for cutting with coagulation in a second monopolar mode.

BACKGROUND

Recently, developments in electrosurgical devices have improved precision cutting to provide for an improved cut over an extended period of time. In these electrosurgical devices, a nonconductive coating, such as glass or ceramic, is applied to leave a minimal trace of exposed metal around the edge (i.e., facets) of a blade electrode. By leaving only a small amount of metal exposed, the electrical energy is focused to the tip of the electrode. Further, these glass and ceramic coatings do not break down as quickly as other nonconductive coatings, such as silicone rubber or PTFE.

While these coated electrodes provide improved cutting, the improvement comes at the cost of other performance characteristics preferred by surgeons. Traditionally, surgeons use the electrosurgical blades to provide for a hemostatic cut, which provides for coagulation. In these improved coated electrode blades, the electrical energy is so focused toward the distal end for a precision cut, the energy is unable to spread outwardly to outward facing sides of the blade to ablate small blood vessels during cutting.

As these coated electrosurgical blades are unable to provide for coagulation, some surgeons now use two separate monopolar devices. A first monopolar device is used for fine controlled dissection. This first monopolar device is a coated electrosurgical blade which provides for precision cutting, allowing for fine controlled dissection. A second monopolar device is then used when a large area of cutting is required in which coagulation is desired. The second monopolar device is a traditional monopolar pencil which allows for faster cutting and coagulation.

Thus what is needed is a single device capable of providing both precision cutting for fine controlled dissection and cutting with coagulation to provide for cutting of larger areas. What is needed is a single device capable of operating in two controlled modes, such as two monopolar modes. What is needed is a device which is able to focus electrical energy to a tip of a blade to provide for precision cutting and is able to focus some electrical energy outward for coagulation.

SUMMARY

The present disclosure relates to an electrosurgical device, comprising: (a) a first pole in the electrosurgical device; and (b) a second pole in the electrosurgical device; wherein the electrosurgical device is operable in either a first monopolar mode or a second monopolar mode; wherein the first monopolar mode is a cut mode utilizing only the first pole; and wherein the second monopolar mode is a cut and coagulation mode utilizing both the first pole and the second pole.

The present disclosure relates to an electrosurgical device comprising: (a) a first pole; (b) a second pole; (c) a blade electrode having: (i) a metal shim having two faces which are generally opposing and one or more facets connecting the two faces; and (ii) a nonconductive coating which covers at least one of the two faces and a portion of the one or more facets of the metal shim, while a distal portion of the one or more facets remains uncovered by the nonconductive coating; (d) a lateral electrode comprised of a broad shim having one or more conductive faces; wherein the broad shim is placed parallel to the blade electrode so that at least one of the one or more conductive faces is exposed and a distal end of the blade electrode protrudes from the lateral electrode, and wherein the lateral electrode is fixed stationary relative to the blade electrode; wherein the nonconductive coating insulates the blade electrode from the lateral electrode; and wherein the first pole is connected to the blade electrode and the second pole is connected to the lateral electrode.

The present disclosure relates to an electrosurgical device comprising: (a) a first pole; (b) a second pole; (c) a blade electrode comprised of: (i) a metal shim having two faces which are generally opposing and one or more facets connecting the two faces; and (ii) a nonconductive coating which covers at least one of the two or more faces and a portion of the one or more facets of the metal shim, while a distal portion of the one or more facets remains uncovered by the nonconductive coating; (d) a lateral electrode comprised of a broad shim, wherein the broad shim is placed parallel to the blade electrode so that a conductive face is exposed and a distal end of the blade electrode protrudes from the lateral electrode, and wherein the lateral electrode has an extended position and a retracted position; wherein the nonconductive coating insulates the blade electrode from the lateral electrode; and wherein the first pole is connected to the blade electrode and the second pole is connected to the lateral electrode.

The present disclosure relates to an electrosurgical device comprising: (a) a first pole; (b) a second pole; (c) a blade electrode comprised of: (i) a metal shim having two or more faces and one or more facets connecting the two or more faces; and (ii) a nonconductive coating which covers at least one of the two or more faces and a portion of the one or more facets of the metal shim, while a distal portion of the one or more facets remains uncovered by the nonconductive coating; (d) a lateral electrode comprised of a broad shim, wherein the broad shim is placed parallel to the blade electrode so that a conductive face is exposed and a distal end of the blade electrode protrudes from the lateral electrode; wherein the blade electrode has an extended position and retracted position relative to the lateral electrode; wherein the nonconductive coating insulates the blade electrode from the lateral electrode; and wherein the first pole is connected to the blade electrode and the second pole is connected to the lateral electrode.

The present disclosure relates to a method for forming an electrosurgical device according to the teachings, the method comprising: (a) coating a metal shim with a nonconductive coating, wherein the metal shim includes at least one face, at least one facet with a distal portion, and a first electrical lead extending from a proximal end, and wherein the nonconductive coating covers the at least one face and the at least one facet; (b) removing the nonconductive coating from a distal portion of the at least one facet; (c) inserting the metal shim into a conductive tube having a second electrical lead extending from a proximal end; and (d) crimping the conductive tube about the shim metal shim to secure the metal shim to the conductive tube.

The present disclosure relates to a method for forming an electrosurgical device according to the teachings, the method comprising: (a) masking a portion of a distal edge portion of a metal shim (b) coating a metal shim with a nonconductive coating, wherein the metal shim includes at least one face, at least one facet with a distal portion, and a first electrical lead extending from a proximal end, and wherein the nonconductive coating covers the at least one face and the at least one facet; (c) removing the mask to expose a distal portion of the at least one facet; (d) inserting the metal shim into a conductive tube having a second electrical lead extending from a proximal end; and (e) crimping the conductive tube about the shim metal shim to secure the metal shim to the conductive tube.

The electrosurgical device of the present disclosure is able to provide for both a fine dissection device and a hemostatic device. A blade electrode may provide fine dissection while a lateral electrode may provide for hemostasis and cutting. The electrosurgical device provides for a single tool which can be used by a surgeon. The blade electrode cooperates with the lateral electrode so that the blade electrode applies a first therapy current and the lateral electrode applies a second therapy current. A first therapy current may be applied for fine dissection and/or precision cutting. A second therapy current or a combination of both the first therapy current and the second therapy current may be applied for cutting with coagulation or hemostasis. A nonconductive coating and/or conductive coating may focus a therapy current or signal to a desired region of the blade electrode, lateral electrode, or both to provide for precise cutting, cutting with coagulation, or both.

BRIEF DESCRIPTION OF DRAWINGS

FIG. 11 is a side view of a blade of an electrosurgical device with the blade in a retracted position according to the teachings.

FIG. 12 is a side view of a blade of an electrosurgical device with the blade in an extended position according to the teachings.

FIG. 13 is a cross-section of the blade electrode of FIG. 12 cut along line A-A.

DETAILED DESCRIPTION

Figures 1, 2:
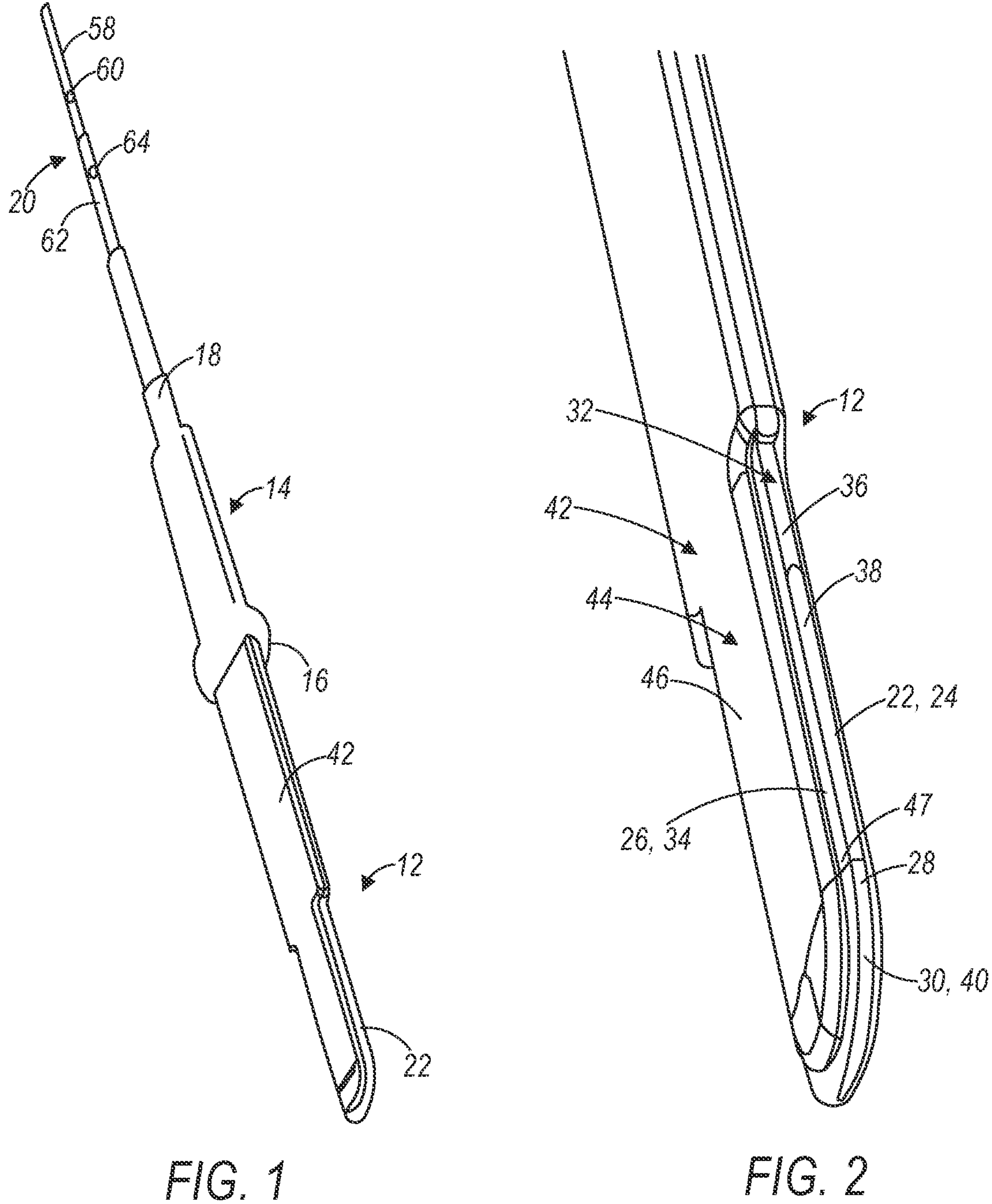
FIG. 1 is a perspective view of an electrosurgical device.
FIG. 2 is a perspective view of a blade of an electrosurgical device.

The explanations and illustrations presented herein are intended to acquaint others skilled in the art with the present teachings, its principles, and its practical application. The specific embodiments of the present teachings as set forth are not intended as being exhaustive or limiting of the present teachings. The scope of the present teachings should be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present teachings relate to an electrosurgical device. The electrosurgical device may include a handpiece. The electrosurgical device may be used by a surgeon to perform a surgical procedure. The electrosurgical device may function to be switched between two or more configurations, two or more modes, or both. For example, the electrosurgical device may be switched between a first monopolar configuration and a second monopolar configuration. In another example, the electrosurgical device may be switched between either a first monopolar configuration or a second monopolar configuration and a dual monopolar configuration. The electrosurgical device may be switched between two or more configurations with a hand of a user. A user may be able to switch between two or more configurations with only a single hand without the need for a second hand, so as to not disrupt a procedure. The electrosurgical device may be used ambidextrously, ambidextrously switched between configurations, or both. The electrosurgical device may be used to cut, perform hemostasis, coagulate, desiccate, fulgurate, electrocautery, or any combination thereof. The electrosurgical device may include monopolar capabilities, bipolar capabilities, non-electrosurgical capabilities, or a combination thereof. The electrosurgical device may be used in open surgery. The electrosurgical device may be used to cut, as a scalpel, or both. The electrosurgical device may include a handpiece and an energy source (e.g., generator). The electrosurgical device may have one or more therapy signals that extend between the handpiece and the energy source.

The electrosurgical device, electrosurgical system, or both may transmit one or more therapy signals. The one or more therapy signals may function to provide power to an electrosurgical device, generate a therapy current, generate one or more monopolar currents, generate one or more bipolar currents, or any combination thereof. The one or more therapy signals may be formed by a handpiece, an energy source (e.g., generator), or both. The therapy signals may be a therapy current. The one or more therapy signals may indicate a user has performed a step and a signal is being transmitted so that therapy current, energy, or both is generated. The one or more therapy signals may provide a signal so that one or more therapy currents are produced. The one or more therapy currents may be used for electrosurgery. The one or more therapy signals may be conducted when an activated circuit is in one or more switch states, the electrosurgical device is one or more configurations, or both. One or more therapy signals may not be generated and/or exit the handpiece when an activation circuit and/or the handpiece is in a non-electrosurgical mode and/or powered off mode, or both. One or more therapy signals may be a monopolar therapy signal, a combination of multiple monopolar therapy signals, bipolar therapy signal, a combination of multiple bipolar therapy signals, or any combination thereof. One or more therapy signals may include a first monopolar therapy signal, a second monopolar therapy signal, or both. The one or more therapy signals may be understood as the therapy signals as described in US Patent Publication No. 2015/0119885, incorporated herein for all purposes.

The electrosurgical device, electrosurgical system, or both may transmit one or more monopolar therapy signals. The monopolar therapy signals may function to provide power to one or more components of the electrosurgical device, may provide a cutting therapy signal, may provide a cutting and coagulating therapy signal, or any combination thereof. A monopolar therapy signal may be any signal that has a voltage differential between a return port and an active port in an energy source (e.g., a generator). A monopolar therapy signal may be any signal that when applied by the electrosurgical device extends from one pole of an electrosurgical device to another pole located at a remote location, off of the electrosurgical device, off the handpiece, or any combination thereof. For example, a monopolar therapy signal may extend from the lateral electrode, blade electrode, or both to one or more return electrodes. The return electrodes may include one or more ground pads. The ground pads may be attached to the patient at a location remote from the surgical site.

A bipolar therapy signal may have a voltage differential between two leads that are connected to the electrosurgical device, located in an energy source (e.g., a generator), or both. A bipolar therapy signal may be a signal that when applied by the electrosurgical device extends from one component of a handpiece to another component of a handpiece. For example, a bipolar therapy signal may be a signal which extends from a lateral electrode to a blade electrode, from a portion of a lateral electrode to another portion of a lateral electrode or both. To switch one or more therapy signals, one or more components of the electrosurgical device may be moved into one or more configurations.

The electrosurgical device may include a plurality of configurations and/or modes. The configurations and/or modes may be any configuration such that the electrosurgical device may be mechanically reconfigured, electrically reconfigured, signally reconfigured and/or different, or any combination thereof. The plurality of configurations and/or modes may include a first monopolar mode, a cut mode, a second monopolar mode, a cut and coagulation mode, a bipolar mode, a non-electrosurgical mode, a powered off mode, or any combination thereof. The electrosurgical device may be transitioned between one or more configurations and/or modes into one or more other configurations and/or mores. At least one of the configurations may apply a therapy current, such as a first therapy current, a second therapy current, or both. Therapy current may include monopolar energy, monopolar current, bipolar energy, bipolar current, or any combination thereof.

The electrosurgical device may transmit monopolar energy or monopolar current. Monopolar energy or current may be any power source that during application extends from one pole of an electrosurgical device to another pole located at a remote location, off of the electrosurgical device, off handpiece, or any combination thereof. Monopolar energy may be energy which extends from one component of the handpiece to a component which is not part of the handpiece. Another pole located at a remote location may include one or more return electrodes. One or more return electrodes may include one or more ground pads. Energy that extends from the blade electrode to a return electrode may be monopolar energy. Energy that extends from the lateral electrode to a return electrode may be monopolar energy. The electrosurgical device may include or operate a plurality of monopolar energy or monopolar current modes. For example, the electrosurgical device may operate in a first monopolar mode, a second monopolar mode, or both. The first monopolar mode may be a cut mode. The first monopolar mode may be useful for applying a therapy current for precision surgical cutting. The second monopolar mode may be a cut and coagulation mode. The second monopolar mode may be useful for applying a therapy current suitable for cutting, coagulating, hemostasis, or any combination thereof.

The electrosurgical device may include a non-electrosurgical configuration. The non-electrosurgical configuration may function as a configuration of the electrosurgical device where no power is supplied to the handpiece, a blade electrode, a lateral electrode, a return electrode, or any combination thereof. The non-electrosurgical configuration of the electrosurgical device may be any configuration where no power is supplied to a handpiece, a blade electrode, a lateral electrode, a return electrode, or any combination thereof. The non-electrosurgical configuration may be used when the electrosurgical device is being used as a scalpel without a therapy current or not being used (i.e., powered off). The non-electrosurgical mode or configuration may be switched to any other configuration by pressing a button, moving a switch, retracting or extending a lateral electrode, retracting or extending a blade electrode, or any combination thereof.

The electrosurgical device may include a first monopolar mode. The first monopolar mode may function to transmit a first therapy current, first monopolar therapy signal, first monopolar current, or any combination thereof. The first monopolar mode may function to concentrate a therapy signal at a distal portion of a blade electrode. The first monopolar mode may be a cut mode. The first monopolar mode may allow a user (i.e., surgeon) to cut tissue, coagulate blood and/or fluids, electrical cutting, hemostasis, apply power to a large area, apply power to a localized area, or any combination thereof. The monopolar mode may provide for precision cutting in a localized area. The first monopolar mode may be used to heat a specific area, heat an object (e.g., tissue) between electrodes, heat an object in contact with the electrodes, or any combination thereof. The first monopolar mode may be used for delicate electrosurgery, localized electrosurgery, coagulation, cutting, or any combination thereof. The first monopolar mode may be used for more delicate procedures, more localized electrosurgery, or both when compared to the second monopolar mode.

In the first monopolar mode, the electrosurgical device may supply power through a handpiece component and a return electrode. The return electrode may be located at another location outside of the handpiece, through a handpiece component and an adjacent handpiece component, or both. In the first monopolar mode, the blade electrode may be in electrical communication with a return electrode. The first monopolar mode may be any configuration where the electrosurgical device may be used to apply monopolar power with the blade electrode. In the first monopolar mode, the blade electrode may at least partially protrude from a lateral electrode, may be extended from or relative to a handpiece and/or lateral electrode, the lateral electrode may be retracted into or relative to the handpiece and/or lateral electrode, or any combination thereof. In the first monopolar mode, the electrosurgical device may only utilize a first pole and a return electrode. In the first monopolar mode, the lateral electrode may be free from receiving a therapy signal, electrical current, power, or any combination thereof. The electrosurgical device may be able to operate the first monopolar mode in sequential series and/or concurrently with a second monopolar mode. The first monopolar mode may be activated by electrically connecting one or more buttons, pressing one or more buttons, moving one or more switches, moving one or more shuttles, electrically connecting all or a portion of an activation circuit, electrically connecting a blade electrode, extending a blade electrode, electrically connecting the blade electrode to a return electrode, electrically disconnecting a lateral electrode, retracting a lateral electrode, or any combination thereof. The first monopolar mode may be deactivated by electrically disconnecting one or more buttons, pressing one or more buttons, moving one or more switches, moving one or more shuttles, electrically disconnecting all or a portion of an activation circuit, electrically disconnecting a blade electrode, retracting a blade electrode, electrically disconnecting a blade electrode to a return electrode, electrically connecting a lateral electrode, extending a lateral electrode, or any combination thereof.

The electrosurgical device may include a second monopolar mode. The second monopolar mode may function to transmit a first therapy current, first monopolar therapy signal, a first monopolar therapy current, a second therapy current, a second monopolar therapy signal, second monopolar current, or any combination thereof. The second monopolar mode may allow for multiple therapy signals and/or currents to be transmitted simultaneously. The second monopolar mode may function to apply a therapy signal to a lateral electrode, blade electrode, or both. The second monopolar mode may be a cut and coagulation mode. The second monopolar mode may allow a user (i.e., surgeon) to cut tissue, coagulate blood and/or fluids, electrical cutting, hemostasis, apply power to a large area, apply power to a localized area, or any combination thereof. The second monopolar mode may provide for cutting and coagulation in a localized area. The second monopolar mode may be used to heat a specific area, heat an object (e.g., tissue) between electrodes, heat an object in contact with the electrodes, or any combination thereof. The second monopolar mode may be used for delicate electrosurgery, localized electrosurgery, coagulation, cutting, or any combination thereof. The second monopolar mode may be used for less delicate procedures, less localized electrosurgery, or both when compared to the first monopolar mode.

In the second monopolar mode, the blade electrode, lateral electrode, or both may be in electrical communication with one or more return electrodes. In the second monopolar mode, the blade electrode may at least partially protrude from a lateral electrode, may be flush with an end of the lateral electrode, may be retracted into a handpiece and/or lateral electrode, the lateral electrode may be extended from and/or relative to the handpiece and/or lateral electrode, or any combination thereof. In the second monopolar mode, the electrosurgical device may utilize a first pole and/or second pole and one or more return electrodes. In the second monopolar mode, the lateral electrode and/or both the lateral electrode and blade electrode may receive a therapy current signal, such as a monopolar therapy signal. In the second monopolar mode, the lateral electrode and/or the blade electrode may transfer a therapy signal to one or more return electrodes. In the second monopolar mode, the blade electrode may transfer a first therapy current, the lateral electrode may transfer a second therapy current, or both to one or more return electrodes. The electrosurgical device may be able to operate the second monopolar mode in sequential series and/or concurrently with a first monopolar mode. The second monopolar mode may be activated by electrically connecting one or more buttons, pressing one or more buttons, moving one or more switches, moving one or more shuttles, electrically connecting all or a portion of an activation circuit, electrically connecting a lateral electrode, electrically disconnecting the blade electrode from a return electrode, extending a lateral electrode, electrically connecting the lateral electrode and/or blade electrode to a return electrode, retracting a blade electrode, or any combination thereof. The second monopolar mode may be deactivated by electrically disconnecting one or more buttons, pressing one or more buttons, moving one or more switches, moving one or more shuttles, electrically disconnecting all or a portion of an activation circuit, electrically disconnecting a lateral electrode, retracting a lateral electrode, electrically disconnecting a lateral electrode from a return electrode, electrically connecting a blade electrode, electrically disconnecting a blade electrode, extending a blade electrode, or any combination thereof.

The electrosurgical device may include a bipolar mode. The bipolar mode may supply power from one portion of the electrosurgical device to a second portion of the electrosurgical device. In the bipolar mode, a distance of the return path for power may be relatively shorter when compared to the distance of one or more return paths of the one or more monopolar modes. The bipolar mode may be any configuration where the electrosurgical device may be used to apply bipolar power. The electrosurgical device in the bipolar mode may supply power between to localized handpiece components, such as a blade electrode, one or more portions of a lateral electrode, or both. The bipolar mode may be used to coagulate, for hemostasis, cutting fulguration, or a combination thereof. In the bipolar mode, the lateral electrode may be extended and/or retracted relative to the handpiece and/or the blade electrode, the blade electrode may be retracted and/or extended relative to the handpiece and/or the blade electrode, the blade electrode may at least partially protrude from the lateral electrode, one or more buttons may be pressed, a shuttle may be moved, or any combination thereof. In the bipolar mode, a bipolar current path may be from the lateral electrode to the blade electrode and/or vice-versa. In the bipolar mode, a bipolar current path may be from one conductive portion (i.e., a conductive face) to another conductive portion (i.e., an opposing conductive face) of the lateral electrode.

The electrosurgical device includes a blade. The blade may function to apply monopolar power during a procedure; apply bipolar power during a procedure; provide a precision cut; provide a large cut; provide hemostasis, coagulation, and/or fulguration; or any combination thereof. The blade includes a blade electrode and a lateral electrode. The blade may be partially located within a handpiece so that a user may manipulate the blade. Some or all of the portion of the blade may be moveable, fixed, or a both relative to the handpiece, other portions of the blade, or both. The blade electrode and lateral electrode may cooperate with one another to provide varying cut styles, coagulation, hemostasis, fulguration, or any combination thereof.

The electrosurgical device includes a blade electrode. The blade electrode may apply monopolar power during a procedure, may be longitudinally moveable, may be rotationally moveable, may be extendable, may be retractable, may be static, may provide a precision cut, may perform hemostasis or coagulation, or any combination thereof. The blade electrode may function as, be electrically connected to, and/or include an electrical pole (i.e., a first pole) of the electrosurgical device. The blade electrode may be static relative to a lateral electrode, a handpiece, or both. The blade electrode may be moveable relative to a lateral electrode, a hand piece, or both. The blade electrode may be parallel to portion of the lateral electrode. One or more faces of the blade electrode may be parallel to one or more faces of the lateral electrode. The blade electrode may be at least partially disposed within a lateral electrode. The blade electrode may at least partially protrude from a lateral electrode. The blade electrode may include a metal shim, a nonconductive (e.g., electrically nonconductive) coating, a conductive (e.g., electrically conductive) coating, a first lead, a first pole, or any combination thereof. The blade electrode may operate in one or more monopolar modes, one or more bipolar modes, or any combination thereof.

The blade electrode may include one or more operating positions. The one or more operating positions may function to conduct a therapy signal, configure the electrosurgical device into a specific mode, or both. The blade electrode may have any suitable position for conducting a therapy signal, configuring the device into a specific mode, or both. The blade electrode may be fixed relative to the lateral electrode, moveable relative to the lateral electrode, fixed relative to the handpiece, moveable relative to the handpiece, or any combination thereof. The blade electrode may have a first monopolar mode position, a second monopolar mode position, bipolar mode position, or any combination thereof. The first monopolar mode position may be any position of the blade electrode suitable for applying a first monopolar current and/or therapy signal. The first monopolar mode position may include the blade electrode partially protruding or exposed from the lateral electrode, a distal portion of the blade electrode protruding or exposed from the lateral electrode, a distal portion of the blade electrode flush or about flush with the lateral electrode, the blade electrode extended relative to the handpiece, the blade electrode fixed relative to the handpiece, the blade electrode extended relative to the lateral electrode, the blade electrode stationary relative to the lateral electrode or any combination thereof. The second monopolar mode position may be any position of the lateral electrode suitable for applying a second monopolar current and/or therapy signal. The second monopolar mode position may include the blade electrode partially protruding or exposed from the lateral electrode, a distal portion of the blade electrode protruding or exposed from the lateral electrode, a distal portion of the blade electrode flush or about flush with the lateral electrode, the blade electrode retracted relative to the handpiece, the blade electrode fixed relative to the handpiece, the blade electrode retracted relative to the lateral electrode, the blade electrode stationary relative to the lateral electrode, or any combination thereof. A bipolar mode operating position may be any one or combination of operating positions of the blade electrode from a first monopolar mode and/or second monopolar mode. Movement, such as retraction and/or extension of the blade electrode may be along a longitudinal axis of the blade, handpiece, lateral electrode, or any combination thereof. The blade electrode may be in communication with or affixed to one or more components which may move the blade electrode relative to the handpiece, lateral electrode or both. The blade electrode may be in communication with or affixed to one or more shuttles, switches, buttons, or a combination thereof which move the blade electrode relative to the handpiece, lateral electrode, or both.

The blade electrode may include a metal shim. The metal shim may provide a precision cut, may conduct a therapy signal, may separate or distance one or more conductive faces of a lateral electrode, or any combination thereof. The metal shim may be any shape to provide a precision cut, a therapy signal, or both. The metal shim may be made of one material or differing materials. The metal shim may include a core material and outer material. The outer material may sandwich the core material. The metal shim may be made of stainless steel, copper, silver, titanium, a metal, a surgical steel, a metal with good thermal dissipation properties, a metal with poor thermal dissipation properties, a material with high thermal conductivity, or any combination thereof. A core material may promote rapid heat transfer of the metal shim. Rapid heat transfer may prevent tissue from sticking and charring during use to the metal shim and/or blade electrode. For example, a distal portion of the metal shim may be made of a core material or expose a core material which promotes rapid heat transfer. An exemplary core material may include copper. An outer material may provide structural strength to the blade electrode. The structural strength may allow the blade to be used for tissue manipulation, such as cutting. An exemplary outer material may include stainless steel. A metal shim comprised of more than one material, having a core material, having an outer material, or any combination thereof may exhibit more rapid cooling than a metal shim comprised of a single material. The metal shim may have a different thermal conductivity than other components of the blade electrode (e.g., nonconductive coating). The metal shim may have a distal end and a proximal end. The proximal end of the metal shim may be located within a hand piece, such as within the channel of the hand piece. The distal end may be opposite the proximal end. The metal shim may be tapered. The metal shim may have distal taper (e.g., metal shim cross section thins from proximal end to distal end), profile taper (e.g., metal shim narrows toward one or more facets), or both. A taper may allow for a distal end of the metal shim to be relatively sharp. By having sharpness, the metal shim may be suitable for cutting tissue even while being powered off (i.e., free of a therapy current).

The metal shim may include two or more faces. The two or more faces may be generally opposing one another. The two or more faces may be distanced from one another. The two or more faces may have a receiving portion passing therethrough. The two or more faces may be joined together by one or more facets, one or more edges, or both. The one or more facets may include one or more facets, two or more facets, three or more facets, four or more facets, or even greater. The one or more facets may be located about at least a portion of the periphery of the metal shim. The one or more facets may project away and/or toward at least one of the two or more faces, project away from a longitudinal axis of the blade, or both. One or more exterior facing surfaces of one or more facets may more an angle relative to an adjacent exterior facing surface of one or more faces. An angle between an exterior surface of a facet and an adjacent exterior surface of a face may be obtuse. The angle between a facet and adjacent exterior surface may allow a distal portion of the blade electrode to be sufficiently sharp to cut tissue. The one or more facets may be substantially planar, nonplanar, or both. The one or more facets may be relatively sharp to provide to allow for cutting of tissue, even if the electrosurgical device is powered off. The one or more facets may connect the one or more faces at one or more edges. One or more edges may be line contact and/or beveled edges between the one or more facets and the one or more faces. The one or more faces, one or more facets, one or more edges, or any combination thereof may be at least partially uncoated, include a nonconductive coating, include a conductive coating, or any combination thereof.

The electrosurgical device includes a nonconductive coating. The nonconductive coating may function to concentrate a therapy signal; provide improved thermal dissipation of a base material; insulate from a therapy signal; prevent corrosion, coat one or more surfaces of a blade electrode, lateral electrode, metal shim, broad shim; or any combination thereof. The nonconductive coating may be an electrically nonconductive coating. The nonconductive coating may cover at least a portion of a lateral electrode, blade electrode, or both. The nonconductive coating may be made of one material or differing materials. The nonconductive coating may be a polymer, elastomeric, silicon, glass, ceramic, silicone rubber, polytetrafluoroethylene (PTFE), chromium, nitride, chromium nitride, alumina, the like, or any combination thereof. The nonconductive coating may extend over all of the blade electrode, a portion of the blade electrode, all of the lateral electrode, and/or a portion of the lateral electrode. The nonconductive coating may extend and cover substantially all of the metal shim, except an active region. The nonconductive coating may extend about a distal portion of the lateral electrode, adjacent an active region. The active region may include one or more facets of the metal shim at a distal end. The active region may include a distal end of the lateral electrode. The active region of the lateral electrode may be flush or about flush with a distal end of the blade electrode, such as when the blade electrode is retracted into the lateral electrode.

Application of the nonconductive coating may include coating a metal shim with the nonconductive coating. The nonconductive coating may be applied to at least one face, one or more facets, a distal portion of one or more facets, or a combination thereof. The nonconductive coating may be removed from at least a portion of the metal shim. Removal may allow one or more surfaces, such as an active region and/or distal portion of at least one facet to be exposed (i.e., not coated with the nonconductive coating). Removal may include physically removing the coating with a solvent, removing a mask, scraping away coating, the like, or a combination thereof. A metal shim may first be masked. A mask may include any removable material which may be removed after application of the nonconductive coating. A mask may include a removable adhesive material, such as a tape. The mask may be specifically applied to surfaces of a metal shim which will remain exposed, such as an active region and/or distal portion of at least one facet.

The nonconductive coating may cover at least one face and a portion of a facet of the metal shim. The nonconductive coating may cover from about 5% to about 95% of a total surface area of the one or more facets of the metal shim. The nonconductive may cover about 50% or more, about 55% or more, or even about 60% or more of a total surface area of the one or more facets of the metal shim. The nonconductive coating may cover about 95% or less, about 90% or less, or even about 85% or less of a total surface area of the one or more facets of the metal shim. The distal portion of the facet may remain uncovered by the nonconductive coating. By having the active region (i.e., distal portion of the facet) remain uncovered, the therapy signal is able to be concentrated toward the distal portion of the facet of the metal shim, the distal end of the lateral electrode, or both. The concentrated therapy signal provides a precision cut.

The nonconductive coating may be located on the blade electrode, lateral electrode, or both in one or more areas where the blade electrode is in direct contact with the lateral electrode. The nonconductive coating may coat one or more receiving channels, one or more faces, or both of the metal shim. The nonconductive coating may coat one or more nonconductive faces, one or more engagement portions, or both of a broad shim and/or lateral electrode. The nonconductive coating may insulate the blade electrode from the lateral electrode. To insulate the blade electrode from the lateral electrode, any surface of the one or more faces of the blade electrode in contact with the lateral electrode may be partially or fully coated with the nonconductive coating. About 70% or greater, about 75% or greater, about 80% or greater, or even about 85% or greater of a surface area of one or more faces of the blade electrode may be coated with the nonconductive coating. About 100% or less, about 95% or less, or even about 90% or less of a surface are of one or more faces of the blade electrode may be coated with the nonconductive coating. To insulate the blade electrode from the lateral electrode and/or prevent direct contact between the metal shim and the broad shim, about 15% to about 95% or even 20% to about 90% of the surface area of the nonconductive coating of the blade electrode may be in direct contact with the lateral electrode. To insulate and prevent direct contact between the metal shim and the broad shim about 70% or greater, about 75% or greater, about 80% or greater, or even about 85% or greater of the surface area of the nonconductive coating of the blade electrode may be in direct contact with the lateral electrode. To insulate and prevent direct contact between the metal shim and the broad shim about 100% or less, about 95% or less, or even about 90% or less of the surface area of the nonconductive coating of the blade electrode may be in direct contact with the lateral electrode. If the lateral electrode has both a retracted position and an extended position, about 15% to about 85% of the surface area of the nonconductive coating of the blade electrode may be in direct contact with the lateral electrode when the lateral electrode is in a retracted position. If the lateral electrode has both a retracted position and an extended position, about 20% to about 90% of the surface area of the nonconductive coating of the blade electrode may be in direct contact with the lateral electrode when the lateral electrode is in an extended position. If the blade electrode has both a retracted position and an extended position, about 15% to about 85% of the surface area of the nonconductive coating of the blade electrode may be in direct contact with the lateral electrode when the blade electrode is in an extended position. If the blade electrode has both a retracted position and an extended position, about 20% to about 90% of the surface area of the nonconductive coating of the blade electrode may be in direct contact with the lateral electrode when the blade electrode is in a retracted position. The nonconductive coating may cooperate with a conductive coating to concentrate a therapy signal.

The electrosurgical device may include a conductive coating. The conductive coating may function to concentrate a therapy signal; provide improved thermal dissipation of a base material; provide structural strength to a base material, insulate from a therapy signal; prevent corrosion, provide a nonstick surface, coat one or more surfaces of a blade electrode, lateral electrode, metal shim, broad shim; or any combination thereof. The conductive coating may cover at least a portion of a lateral electrode, blade electrode, or both. The conductive coating may be made of one material or differing materials. The conductive coating may be made of ceramic, titanium, nitride, titanium nitride, the like, or any combination thereof. The conductive coating may extend about a portion of the metal shim. The conductive coating may coat an active region of the metal shim, lateral electrode, or both. The active region may include one or more facets, one or more faces, one or more edges, or any combination thereof of the metal shim at a distal end. The active region may include a distal end of the lateral electrode. The active region of the distal end of the lateral electrode may be adjacent to the blade electrode, to active region of the blade electrode, or both. The active region of the lateral electrode may be flush or about flush with a distal end of the blade electrode, such as when the blade electrode is retracted into the lateral electrode. The conductive coating may be spaced from and/or adjacent to the nonconductive coating. The conductive coating may cover about 5% or more, about 10% or more, or even about 15% or more of a surface area of one or more facets. The conductive coating may cover about 50% or less, about 45% or less, about 40% or less, or even about 35% or less of one or more facets.

The blade electrode may include a receiving portion. The receiving portion may function to engage the blade electrode with the lateral electrode, affix the lateral electrode to the blade electrode, cooperate with the lateral electrode, move the blade electrode, move the lateral electrode, or any combination thereof. The receiving portion may have any size, shape, and/or be located anywhere in the blade electrode to allow the blade electrode to engage the lateral electrode, affix the lateral electrode to the blade electrode, allow the blade electrode to cooperate with the lateral electrode, move the blade electrode, move the lateral electrode, or any combination thereof. The receiving portion may include one or more tracks, grooves, notches, indents, the like, or any combination thereof. The receiving portion may be a track along the longitudinal axis of the blade. The track may extend partway or through the thickness of the blade electrode. The receiving portion may receive an engagement portion of the lateral electrode. The receiving portion may allow the engagement portion to move relative to the receiving portion, the receiving portion to slide relative to the engagement portion, or both. The receiving portion may allow the blade electrode, lateral electrode, or both to be placed into one or more operation positions. The receiving portion may be electrically insulated from the lateral electrode. The receiving portion may at least be partially or completely coated in a nonconductive coating. Any surface of the receiving portion which may contact a surface of the lateral electrode in either an extended position or retracted position may be coated with a nonconductive (e.g., electrically nonconductive) coating.

The electrosurgical devices includes a lateral electrode. The lateral electrode may apply monopolar power during a procedure, may be longitudinally moveable, may be rotationally moveable, may be extendable, may be retractable, may be static, may provide a cut, may perform hemostasis or coagulation, or any combination thereof. The lateral electrode may function as, be electrically connected to, and/or include an electrical pole (i.e., a second pole) of the electrosurgical device. The lateral electrode may be static relative to a blade electrode, a handpiece, or both. The lateral electrode may be moveable relative to a blade electrode, a handpiece, or both. The lateral electrode may be at least partially parallel to a portion of the blade electrode. The lateral electrode may partially surround, partially encircle, completely surround, complete encircle, or any combination thereof the blade electrode. The lateral electrode may allow at least part of the blade electrode to protrude therefrom. The lateral electrode may include a broad shim, a nonconductive coating, a second lead, a second pole, or any combination thereof.

The lateral electrode includes a broad shim. The broad shim may provide a cut, coagulation, may conduct a therapy signal, or any combination thereof. The broad shim may be any shape to provide a cut, a therapy signal, coagulation, partially surround the blade electrode, or any combination thereof. The broad shim may be made of one material or differing materials. The broad shim may be made of stainless steel, copper, silver, titanium, a metal, a surgical steel, a metal with good thermal dissipation properties, a metal with poor thermal dissipation properties, a material with high thermal conductivity, or any combination thereof. The broad shim may be tubular prior to being engaged with the blade electrode, metal shim, or both. The broad shim may be a conductive tube. The conductive tube may partially or fully encircle and/or surround the blade electrode. The broad shim may be crimped about the blade electrode, metal shim, or both. The broad shim may include one or more cut-outs. The one or more cut-outs may allow at least a portion of two or more faces, one or more facets, a distal portion of one or facets or a combination thereof to be exposed. The exposed faces, facets, or both may project outwardly (e.g., distally) from the broad shim (e.g., conductive tube). The broad shim may include at least two conductive faces. The at least two conductive faces may be distanced from one another, generally parallel, or both. The at least two conductive faces may be generally parallel to the at least two faces of the metal shim. The at least two conductive faces may be connected with an engagement portion. The broad shim may partially surround, partially encircle, completely surround, complete encircle, or any combination thereof the metal shim. The broad shim may have a different thermal conductivity than other components of the lateral electrode (e.g., nonconductive coating, conductive coating). The broad shim may have a distal end and a proximal end. The proximal end of the broad shim may be located within a handpiece, such as within the channel of the handpiece. The distal end may be opposite the proximal end.

The lateral electrode may include an engagement portion. The engagement portion may function to engage the lateral electrode with the blade electrode, affix the lateral electrode to the blade electrode, cooperate with the blade electrode, move the lateral electrode, move the blade electrode, or any combination thereof. The engagement portion may have any size, shape, and/or be located anywhere in the lateral electrode to allow the lateral electrode to engage with the blade electrode, affix the lateral electrode to the blade electrode, allow the lateral electrode to cooperate with the blade electrode, move the lateral electrode, move the blade electrode, or any combination thereof. The engagement portion may include one or more protrusions, extensions, a T-shape insert, I-shape insert, H-shape insert, the like, or any combination thereof. The engagement portion may connect two or more conductive faces of the lateral electrode. The engagement portion may allow the conductive faces to be on opposing sides of the blade electrode. The engagement portion may be located along the or parallel to the longitudinal axis of the lateral electrode. The engagement portion may be located along an interior of the lateral electrode. The engagement portion may be located at and/or extend from one or more faces of the lateral electrode which are parallel and facing toward the blade electrode. The engagement portion may be inserted into the receiving portion, such as a track, along the longitudinal axis of the blade electrode. The engagement portion may allow the receiving portion to move relative to the engagement portion, the engagement portion to slide relative to the receiving portion, or both. The engagement portion may allow the lateral electrode, blade electrode, or both to be placed into one or more operation positions. The engagement portion may be electrically insulated from the blade electrode. The engagement portion may be partially or completely coated with a nonconductive coating. Any surface of the engagement portion which may contact a surface of the blade electrode in either an extended position or retracted position may be coated with a nonconductive (e.g., electrically nonconductive) coating.

The lateral electrode may include one or more operating positions. The one or more operating positions may function to conduct a therapy signal, configure the electrosurgical device into a specific mode, or both. The lateral electrode may have any suitable position for conducting a therapy signal, configuring the device into a specific mode, or both. The lateral electrode may be fixed relative to the blade electrode, moveable relative to the blade electrode, fixed relative to the handpiece, moveable relative to the handpiece, or any combination thereof. The lateral electrode may have a first monopolar mode position, a second monopolar mode position, a bipolar mode position, or any combination thereof.

A first monopolar mode position may be any position of the lateral electrode suitable for applying a first monopolar current and/or therapy signal, being free of a monopolar current and/or therapy signal, or both. The first monopolar mode position may include the lateral electrode partially exposing part of the blade lateral electrode, a distal portion of the lateral electrode exposing a distal portion of the blade electrode, a distal portion of the lateral electrode flush or about flush with the distal portion of the blade electrode, the lateral electrode retracted relative to the handpiece, the lateral electrode fixed relative to the handpiece, the lateral electrode retracted relative to the blade electrode, the lateral electrode stationary relative to the blade electrode or any combination thereof.

A second monopolar mode position may be any position of the lateral electrode suitable for applying a second monopolar current and/or therapy signal. The second monopolar mode position may include the lateral electrode partially exposing the lateral electrode, a distal portion of the lateral electrode exposing a distal portion of the blade electrode, a distal portion of the lateral electrode flush or about flush with a distal portion of the blade electrode, the lateral electrode extended relative to the handpiece, the lateral electrode fixed relative to the handpiece, the lateral electrode extended relative to the blade electrode, the lateral electrode stationary relative to the blade electrode, or any combination thereof.

A bipolar mode operating position may be any one or combination of operating positions of the lateral electrode from a first monopolar mode and/or second monopolar mode. Movement, such as retraction and/or extension of the lateral electrode may be along a longitudinal axis of the blade, handpiece, blade electrode, or any combination thereof. The lateral electrode may be in communication with or affixed to one or more components which may move the lateral electrode relative to the handpiece, blade electrode or both. The lateral electrode may be in communication with or affixed to one or more shuttles, switches, buttons, or a combination thereof which move the lateral electrode relative to the handpiece, blade electrode, or both.

The electrosurgical device may include two or more leads. The two or more leads may function to electrically connect the electrosurgical device, the blade electrode, the lateral electrode, or any combination thereof to an electrosurgical system, an energy source, a return electrode, or any combination thereof. The two or more leads may function to house one or more electrical poles. The two or more leads may transmit power, such as monopolar or bipolar power, a monopolar or bipolar current, a monopolar therapy signal, a bipolar therapy signal, or any combination thereof. The two or more leads may transmit information, such as the activation (i.e., pressing of buttons, movement of a shuttle) of one or more switches. The two or more leads may be in electrical communication, direct contact, or both with one or more electrical circuit switches. Electrical continuity between one or more witches and one or more leads may result in a central processing unit relaying information to an energy source, an energy source providing a therapy signal and/or current to one or more leads, or both. The two or more leads may extend from the blade electrode, the lateral electrode, or both. For example, a first lead may extend from the blade electrode, a second lead may extend from the lateral electrode or both. One or more leads may be electrically insulated from one or more other leads. One or more leads may include insulation between one or more other leads. For example, the two or more leads may be in the form of or within a coaxial cable. The coaxial cable may include an insulation between the first lead and the second lead.

The electrosurgical device may include a shuttle. The shuttle may function as a control device and/or an actuator or be part of a control device and/or actuator. The shuttle may function to cover one or more buttons, move a blade electrode, move a lateral electrode, immobilize and/or electrically disconnect one or more features of the electrosurgical device and/or activation circuit, immobilize one or more buttons, impede movement and/or depression of one or more buttons, or any combination thereof. The shuttle may have any shape and/or size to cover one or more buttons, move a blade electrode, move a lateral electrode, immobilize and/or electrically disconnect one or more features of the electrosurgical device and/or activation circuit, immobilize one or more buttons, impede movement and/or depression of one or more buttons, or any combination thereof. The shuttle may be a shield that covers one or more buttons. The shield may cover one or more buttons which are not in use. The shield may cover one or more buttons so that the one or more buttons are protected from contact (e.g., prevented from being pressed). For example, when the electrosurgical device is in a first monopolar mode configuration, the shuttle may cover a button to prevent activation of a second monopolar mode, expose a button to activate a first monopolar mode, and/or vice-versa. The shuttle may be a solid piece. The shuttle may include a device that extends under, around, through, or any combination thereof one or more buttons so that movement of the one or more buttons is impeded, prevented, or both. For example, when the shuttle is moved, a portion of the shuttle may extend under one or more buttons so that a user is unable to depress the button to provide power, electricity, a therapy current, or any combination thereof. The shuttle may include one or more positions. The shuttle may have a first position and a second position. The shuttle may be in a first position when the electrosurgical device is in a first monopolar configuration. The shuttle may be in a second position when the electrosurgical device is in a second monopolar configuration. The shuttle in the first position, second position, or both may perform any of the functions discussed herein for the shuttle. The shuttle may be moved by sliding on a track. The shuttle may move, or be part of an assembly that moves, the blade electrode, the lateral electrode, or both. The shuttle may retract and/or extend the blade electrode, the lateral electrode, or both relative to a handpiece.

The shuttle may be connected to one or more components of the electrosurgical device which may be retracted, extended, or both. For example, the shuttle may be connected with the lateral electrode, blade electrode, or both. The shuttle may be used to move the lateral electrode, blade electrode, or both between monopolar configurations. Movement of the shuttle toward the distal end of the hand piece may result in one or more components of the electrosurgical device being extended from the handpiece. For example, movement of the shuttle toward the distal end of the hand piece may result in the lateral electrode, blade electrode, or both extending relative to the handpiece. Movement of the shuttle toward the proximal end of the handpiece may result in one or more components of the electrosurgical device being retracted into the hand piece. For example, movement of the shuttle toward the proximal end of the handpiece may result in the lateral electrode, blade electrode, or both retracting relative to the handpiece. The shuttle may be integrally connected with the blade electrode, lateral electrode, or both. The shuttle may be connected to the handpiece. The shuttle may be located within a track, such as track within the handpiece. The shuttle may be connected to the handpiece and slide on a track of the handpiece.

The electrosurgical device may include one or more buttons. The one or more buttons may function as a control device and/or actuator or be part of a control device and/or actuator. The one or more buttons may function to control one or more functions of the electrosurgical device. The one or more buttons may control a monopolar power, bipolar power, a first monopolar mode, a second monopolar mode, a cut mode, a cut and coagulation mode, a therapy current, movement of a blade electrode, movement of a lateral electrode, or any combination thereof. The one or more buttons may be in electrical contact, direct contact, or both with one or more electrical switches. Pressing of a button may result in an electrical switching closing or opening an electrical circuit. The one or more buttons may include a first button, a second button or both. The one or more buttons may include two buttons. The one or more buttons may have any size and/or shape and may be located anywhere to allow a user (i.e., surgeon) to control one or more functions of the electrosurgical device. One or more buttons may have a color and/or configuration to control a first monopolar mode, a cut mode, or both. For example, a first button may control a first monopolar mode, a cut mode, or both. One or more buttons may have a color and/or control a second monopolar mode, a cut and coagulation mode, or both. For example, a second button may control a second monopolar mode, a cut and coagulation mode, or both. One or more buttons may be exposed and/or unlocked by a shuttle when the shuttle moves, the blade electrode moves, the lateral electrode moves, or any combination thereof. One or more buttons may be covered and/or locked by a shuttle when the shuttle moves, the blade electrode moves, the lateral electrode moves, or any combination thereof. For example, a first button may only be exposed when the shuttle, the lateral electrode, the blade electrode, or any combination thereof are in a first monopolar mode, a cut mode, or both. For example, a second button may only be exposed when the shuttle, the lateral electrode, the blade electrode, or any combination thereof are in a second monopolar mode, a cut and coagulation mode, or both. One or more buttons may turn on power to a respective electrode so that power is supplied to an area of interest. For example, a first button may turn power on to the blade electrode. For example, a second button may turn power on to the blade electrode, lateral electrode, or both. The one or more buttons may be a single button. A single button may include a selector.

The selector may allow a user (i.e., surgeon) to control and/or select one or more functions of the electrosurgical device. The selector may allow a user to select from a first monopolar mode, cut mode, second monopolar mode, cut and coagulation mode, or any combination thereof. The selector may be automatically moved when the blade electrode, lateral electrode, or both are extended and/or retracted. The user may set the selector to a desired mode and/or function. A selector may power one or more functions and/or modes simultaneously. The electrosurgical device may include a button that locks the configuration of the blade electrode and/or lateral electrode. The electrosurgical device may include a button that allows movement of the blade electrode and/or lateral electrode. The selector, one or more buttons, or both may be part of a handpiece.

The electrosurgical device may include a handpiece. The handpiece may function to provide a handgrip for a user of the device; house one or more control buttons, house one or more switches, or any combination thereof. The handpiece may house the lateral electrode, blade electrode, or both. The handpiece may house one or more leads, one or more diodes, one or more coaxial cables, one or more diodes, one or more capacitors, or any combination thereof. The handpiece may house all or a portion of the control circuity, a central processing unit, or both. The handpiece may electrically connect the electrosurgical device, the electrical system, or both to an energy source (e.g., a generator). The handpiece may physically connect the functional elements of the electrosurgical device, electrically connect the electrical elements of the electrosurgical device, or both. The handpiece may have any size and/or shape suitable for providing a handgrip. The handpiece may have any size and/or shape suitable for housing one or more control buttons house one or more switches, house a lateral electrode, house a blade electrode, house one or more electrical components, or any combination thereof. The handpiece may be or include a portion a user (i.e., surgeon) grips to hold the electrosurgical device. The handpiece may be or include a portion a user (i.e., surgeon) uses to move a switch, such as to move a portion of the electrosurgical device (i.e., lateral electrode and/or blade electrode) into a retracted position, extended position, or both. The handpiece may be or include a portion a user (i.e., surgeon) uses to press one or more buttons to apply power to a desired location (i.e., a first monopolar mode, second monopolar mode, or both). The handpiece may be a central portion that includes both one or more buttons and one or more electrical connectors for supplying power to the electrosurgical device, the blade electrode, the lateral electrode, or any combination thereof. The handpiece may include the lateral electrode, blade electrode, or both within a channel.

A hand piece of the electrosurgical device may include a channel. The channel may function to house a lateral electrode, blade electrode, or both. The channel may allow the lateral electrode, blade electrode, or both to retract and/or extend from the channel. The channel may have any size and/or shape to house the lateral electrode, blade electrode, or both; allow the lateral electrode, blade electrode, or both to retract and/or extend from the channel; or any combination thereof. The channel may be located centrally within the handpiece. The channel may extend from a distal end of the handpiece toward a proximal end of the handpiece. The channel may be located within the handpiece. The channel may be an absence of material so that the blade electrode, lateral electrode, or both may be located within the channel, retract from the channel, extend from the channel, or any combination thereof. The channel may be in communication with one or more switches, one or more control buttons, or both. The channel may be any shape to house one or more components of the electrosurgical device. The channel may be round, square, oval, diamond, the like, or any combination thereof. The channel may be a key slot.

The blade electrode, the lateral electrode, or both may complete a circuit when in contact with tissue. The tissue may electrically connect the blade electrode, the lateral electrode, or both to one or more return electrodes. The tissue may electrically connect opposing conductive faces of the lateral electrode, such as when in a bipolar mode. The tissue may act as an electrical bridge between the blade electrode, lateral electrode, or both and one or more return electrodes. Movement of the lateral electrode, blade electrode, one or more buttons, a shuttle, or any combination thereof may activate a circuit, a switch, or both.

The electrosurgical device may be part of an electrical circuit. The circuit may have one or more switches that switch between one or more monopolar modes, a bipolar mode, a cut mode, a cut and coagulation mode, a non-electrosurgical mode, a powered off mode, or any combination thereof. One or more switches may activate one or more monopolar electrodes (i.e., blade electrode, lateral electrode, or both), activate one or more return electrodes (i.e., one or more ground pads), or both. One or more switches may activate one or more bipolar electrodes, deactivate one or more return electrodes, or both. One or more switches may deactivate one or more monopolar electrodes, one or more bipolar electrodes, one or more return electrodes, or any combination thereof. The blade electrode, lateral electrode, one or more return electrodes, or any combination thereof may be connected to an energy source. The energy source may be an alternating current power source or a direct current power source.

The electrosurgical device may include one or more power connectors. The power connectors may function to supply power, a therapy current or both from an energy source to an electrosurgical system, the electrosurgical device, or both so that the electrosurgical device may be used for electrosurgery. The electrosurgical system, electrosurgical device, the handpiece, or any combination thereof may include one or more or two or more power connectors supplying power to the electrosurgical system, electrosurgical device, handpiece, or any combination thereof. The therapy current may be any current that is applied by the electrosurgical device and performs a predetermined function. The therapy current may be monopolar power, bipolar power, cutting, coagulation, hemostasis, or any combination thereof. The therapy current may be any application of power that is produced by the electrosurgical device. The therapy current may be any application of power that extends into and through the electrosurgical device from one or more power connectors. The therapy current may be supplied from a voltage source. The voltage source may be any supply of energy that performs one or more functions discussed herein. The voltage source may be a direct current voltage source or an alternating current voltage source. The power connectors may be wires, pieces of a conductor, or both.

The electrosurgical device may include one or more power connectors, two or more power connectors, three or more power connects, or even four or more power connectors. For example, in a three power connector system, the power connectors may be and/or connected to a positive pin, a negative pin, a return pin, or any combination thereof. For example, in a four power connector system, the power connectors may be and/or connected to a bipolar positive pin, a bipolar negative pin, a monopolar active pin, a monopolar return pin, or any combination thereof. Each of the power connectors may be directly connected to an energy source, such as a generator.

The electrosurgical device may be connected to or include an energy source. The energy source may function to supply power, a therapy current, control signals, an electrosurgical therapy signal, or any combination thereof. The energy source may be any device that functions to supply power, a therapy current, control signals, an electrosurgical therapy signal, or any combination thereof. The energy source may be a generator. The energy source may electronically reconfigure itself in response to a signal from a user, physically reconfigure itself in response to an adjustment by a user, or both. The energy source may function to be electrically connected to a handpiece to provide and/or receive electrosurgical therapy signals, power therapy current, or any combination thereof. The energy source may be capable of producing only a single therapy current, two therapy currents, more than two therapy currents, or any combination thereof. The energy source may include two or more power connections, three or more power connections, or four or more power connections. The power connections may be any port in the generator so that one or more power connectors of a handpiece may be plugged into so that power, control signals, therapy currents, or any combination thereof are supplied to the electrosurgical device. The energy source may include one or more switches that may be switched between one or more power connections so that power, signals, or both may be selectively applied to the electrosurgical device based upon a desired configuration of the electrosurgical device.

The electrosurgical device may be connected to or include a central processing unit (CPU), a series of internal switching or both. The internal switching may provide a signal from an activation circuit to the energy source so that the energy source supplies power to the electrosurgical device, such as the handpiece. The central processing unit may be interchanged with the internal switching and switching may perform the same functions as the central processing unit. The central processing unit may be any device that provides power, signals, electrical reconfiguration, a switch between two or more therapy currents, a switch between two or more configurations or modes, a switch between two or more therapy signals, or any combination thereof so that the electrosurgical device may perform a desired function. The central processing unit may be used to switch the electrosurgical device between a first monopolar mode, a second monopolar mode, a cut mode, a cut and coagulation mode, a bipolar mode, or any combination thereof. The central processing unit may be in electrical communication with one or more switches, one or more poles, an energy source, or any combination thereof. The central processing unit may in electrical communication with one or more switches which may be in electrical communication with one or more poles. For example, the central processing unit may be in electrical communication with a first switch, a second switch, or both. The central processing unit may determine continuity between one or more switches and one or more poles. The central processing unit may direct an energy source to supply power to one or more poles based on electrical continuity between one or more switches and one or more poles. The central processing unit may determine whether a single therapy signal needs to be transmitted or multiple therapy signals need to be transmitted. For example, if there is electrical continuity between only one pole and one switch, a single therapy signal may be transmitted. The single therapy signal may be a first monopolar therapy signal. For example, if there is electrical continuity between a first pole and a first switch and also electrical continuity between a second pole and a second switch, two therapy signals may be transmitted. The two therapy signals may include a first monopolar therapy signal and a second monopolar therapy signal.

The electrosurgical device may be connected to one or more switches. The one or more switches may function to open and/or close a circuit, provide electrical continuity, deliver electrical energy, divert electrical energy, or any combination thereof. The switches may have any shape, function, and/or be anywhere in a circuit of the electrosurgical device, electrosurgical system, or both to open and/or close a circuit, provide electrical continuity, deliver electrical energy, divert electrical energy, or any combination thereof. The one or more switches may be in electrical communication with an energy source, a central processing unit, one or more buttons, one or more poles, one or more leads, or any combination thereof. Any component of the electrosurgical device and/or electrosurgical system may function to close and/or open the one or more switches. For example, one or more buttons may be in electrical communication and/or in directly connected to the one or more switches. Depressing of one or more buttons may result in the one or more switches opening and/or closing. When closed, the one or more switches may provide electrical continuity between one or more poles, the central processing unit, and/or an energy source. Closing of one or more switches may result in one or more therapy signals being transmitted from the energy source to the handpiece, one or more poles, one or more leads, the lateral electrode, the blade electrode, or any combination thereof. Closing of one or more switches may result at least one monopolar therapy signal being delivered. The one or more switches may include a first switch and a second switch. The first switch may be in electrical communication with a first pole, the second switch may be in electrical communication a second pole, or both. Closing of a first switch may result in electrical continuity between the first switch and the first pole and/or between the first switch and the second pole. Closing of a second switch may result in electrical continuity between the second switch and a second pole and/or between the second switch and the first pole. Closing of a single switch (e.g., first switch and/or second switch) may result in electrical continuity between the single switch and a single pole or a plurality of poles (e.g., first and second pole). Closing of a single switch (e.g., first switch and/or second switch) may result in electrical continuity between an energy source and a single pole (e.g., first or second pole) or a plurality of poles (e.g., first and second pole). Closing of a single switch (e.g., first switch and/or second switch) may result in electrical continuity between an energy source and the first pole, between the energy source and the second pole, or both. If more than one switch is closed, at least one switch may divert a portion or all of an electrical signal. By diverting a portion or all of an electrical signal, the handpiece may receive more than one therapy signal. For example, the energy source may transmit an electrical energy signal to the one or more switches and if more than one switch is closed, a portion of the electrical energy signal may be diverted to multiple poles through at least one of the switches.

The electrosurgical device, the electrosurgical system, or both may include a plurality of poles. The poles may function to receive a therapy current from one or more energy sources, control the direction (e.g., flow) of a therapy current in an electrosurgical device and/or system, or both. The plurality of poles may direct one or more therapy currents from a single energy source to one or more return electrodes. The plurality of poles may have any configuration to receive a therapy current from one or more energy sources; transmit a therapy current to a handpiece, blade, blade electrode, lateral electrode, return electrode, or a combination thereof; or both. The plurality of poles may be located anywhere within an electrosurgical device and/or electrosurgical system. The plurality of poles may be located within a handpiece, a coaxial able, a first and/or second lead, a blade, a blade electrode, a lateral electrode, a return electrode, or any combination thereof. The plurality of poles may include one or more active poles and one or more return poles. One or more poles may have a same or different polarity as one or more other poles. The plurality of poles may include a first pole, a second pole, and a return pole. A first pole may be in communication with, connected to, and/or part of a blade electrode and/or a first lead. A second pole may be in communication with, connected to, and/or part of a lateral electrode and/or a second lead. A return pole may be in communication with, connected to, and/or part of an electrosurgical system, energy source, or both. A ground pole may be considered as or part of a return electrode. A first pole may have a same or different polarity as a second pole. The first pole may direct a first therapy current from an energy source to a return electrode. The second pole may direct a second therapy current from an energy source to a return electrode. The first pole may direct the first therapy current to the same or a different return electrode as the second pole directs the second therapy current to.

The electrosurgical device, the electrosurgical system, or both may include one or more return electrodes. The one or more return electrodes may function to receive a therapy current from one or more poles, the handpiece, the blade, the blade electrode, the lateral electrode, or any combination thereof and/or return the therapy current to an energy source. The one or more return electrodes may have be any configuration to receive a therapy current from one or more poles, the handpiece, the blade, the blade electrode, the lateral electrode, or any combination thereof and/or return the therapy current to an energy source. The one or more return electrodes may include one or more ground pads. The one or more return electrodes may be in electrical communication with an energy source via a common return path, separate return paths, or a combination of both. The one or more return electrodes may be in electrical communication with one or more switches. The one or more switches may allow the one or more return electrodes to transmit one or more therapy signals to the energy source. Electrical continuity between one or more return electrodes and an energy source through a closed switch may allow the one or more return electrodes to transmit one or more therapy signals to the energy source. Electrical discontinuity between one or more return electrodes and an energy source through an open switch may prevent the one or more return electrodes from transmitting one or more therapy signals to the energy source.

The electrosurgical device, the electrosurgical system, or both may include a return path from the one or more return electrodes to an energy source. The return path may function to transmit and/or prevent transmission of a therapy current from one or more return electrodes to an energy source. The return path may have any configuration to transmit and/or prevent transmission of a therapy current from one or more return electrodes to an energy source. The return path may be directly connected to one or more return electrodes, an energy source, and/or may include one or more switches therebetween.

The electrosurgical device, the electrosurgical system, or both may be configured into or create various circuits by electrically configuring one or more components of the electrosurgical device, physically configuring one or more components of the electrosurgical device, or both. The various circuits may include a first monopolar circuit, a first signaling circuit, a second monopolar circuit, a second signaling circuit, a dual monopolar circuit, a bipolar circuit, or any combination there. During use, one or more switches may be opened and/or closed so that one or more open circuits, one or more closed circuits, or both may be formed. For example, a blade electrode may be extended, a lateral electrode may be retracted, a shuttle may be moved forward, and/or one or more buttons may be pressed so that an electrical connection is formed between the blade electrode, an energy source, and a return electrode so that a first monopolar circuit is completed. The blade electrode, energy source, and return electrode may form a circuit in the first monopolar mode to provide a path for a monopolar current and/or monopolar therapy signal. For example, a blade electrode may be retracted, a lateral electrode may be extended, a shuttle may be moved rearward, and/or one or more buttons may be pressed so that an electrical connection is formed between the blade electrode, an energy source, and a return electrode and an electrical connection is formed between the lateral electrode, the energy source, and a return electrode. The blade electrode, an energy source, and a return electrode may form one electrical circuit, such as a first monopolar circuit and/or signaling circuit. The first monopolar circuit and/or first signaling circuit may provide a path for a monopolar current or therapy signal during the first monopolar mode. The lateral electrode, the energy source, and a return electrode may form another electrical circuit, such as a second monopolar circuit and/or second signaling circuit. The second monopolar circuit and/or second signaling circuit may include or exclude the blade electrode. The second monopolar circuit and/or second signaling circuit in the second monopolar mode to provide a path for a monopolar current and/or monopolar therapy signal.

The present teachings also relate to a method of switching the electrosurgical device from one mode to another mode, such as from one monopolar modes to another monopolar mode, to a bipolar mode, to a non-electrosurgical mode, to a powered off mode, or a combination thereof. The method may include one or more of the steps discussed herein in virtually any order. The method may include retracting and/or extending the lateral electrode, retracting and/or extending the blade electrode, moving a shuttle, pressing one or more buttons, applying a return electrode, removing a return electrode, reconfiguring a circuit, or any combination thereof. The method may include a step of applying a first monopolar current and/or therapy signal and then immediately subsequently applying a second monopolar current and/or therapy signal. The method may include a step of simultaneously applying a first monopolar current and/or therapy signal with a second monopolar current and/or therapy signal. The method may include a step of apply a first and/or second monopolar current and/or therapy signal subsequently and then immediately subsequently applying a bipolar current and/or therapy signal or vice-versa. The method may include a step of powering on and/or power off the electrosurgical system, electrosurgical device, or both. The method may include a step of cutting (i.e., precise) in a non-electrosurgical configuration or in a first monopolar mode, then applying another monopolar power (i.e., in the second monopolar mode) or bipolar power to coagulate, cauterize, and/or continue cutting, or both with a step of changing instruments.

ILLUSTRATIVE EMBODIMENTS

The following descriptions of the Figures are provided to illustrate the teachings herein, but are not intended to limit the scope thereof. Features of one embodiment may be employed in another embodiment. For example, any of the features of FIGS. 8 through 13 may be incorporated into any of the embodiments as shown in FIGS. 1 through 7 and vice-versa; any of the features of FIGS. 8 through 10 may be incorporated into any of the embodiments as shown in FIGS. 11 through 13 and vice-versa; any of the features as shown in FIGS. 14 through 18 may be incorporated with any of the embodiments of FIGS. 1 through 13; and any of the features as shown in FIGS. 14 through 18 may be incorporated with any of the other features of FIGS. 14 through 18.

FIG. 1 illustrates a perspective view of an electrosurgical device 10. The electrosurgical device 10 includes a blade 12 attached to a handpiece 14. The handpiece 14 is a handle or grip for a user to hold and manipulate the electrosurgical device 10. The handpiece 14 includes a channel 16, such as a key slot which receives the blade 12. The blade 12 includes a blade electrode 22. The blade electrode 22 is attached to a first lead 58 having a first pole 60. The blade electrode 22 is partially surrounded by a lateral electrode 42. The lateral electrode 42 is attached to a second lead 62 having a second pole 64. The first lead 58 and the second lead 62 are part of a coaxial cable 20 which extends from a proximal end 18 of the hand piece 14.

FIG. 2 illustrates a blade 12 of an electrosurgical device 10. The blade 12 includes a blade electrode 22. The blade electrode is a metal shim 24. The metal shim 24 includes opposing metal shim faces 26 connected by a metal shim facet 28. The metal shim 24 includes a distal end 30 opposite the handpiece 14 (not shown). The metal shim 24 is partially covered in a nonconductive coating 32. The nonconductive coating 32 coats the metal shim faces 26 to provide for coated metal shim faces 34. The nonconductive coating 32 coats part of the metal shim facet 28 to provide for coated metal shim facet 36 and exposed metal shim facet 38. The exposed metal shim facet 38 includes the facet at the distal end 30 to provide for a distal end exposed metal shim facet 40. The blade electrode 22 is partially surrounded by a lateral electrode 42. The lateral electrode 42 includes a broad shim 44. The broad shim 44 includes conductive faces 46. The conductive faces 46 face outwardly and are generally parallel to the coated metal shim faces 34. Opposing the conductive faces 46, the broad shim 44 includes interior faces 47. The interior faces 47 are located parallel to the coated metal shim faces 34. Only part of the blade electrode 22 is in direct contact with the lateral electrode 42, so that at least part of the coated metal shim faces 34, coated metal shim facet 36, and exposed metal shim facet 38 protrude out of the lateral electrode 42. The only direct contact between the blade electrode 22 and the lateral electrode 42 includes the nonconductive coating 32. There is no direct contact between the metal shim 24 (i.e., exposed metal shim, metal shim without nonconductive coating) and the broad shim 44 (i.e., exposed broad shim, broad shim without nonconductive coating).

Figure 3:
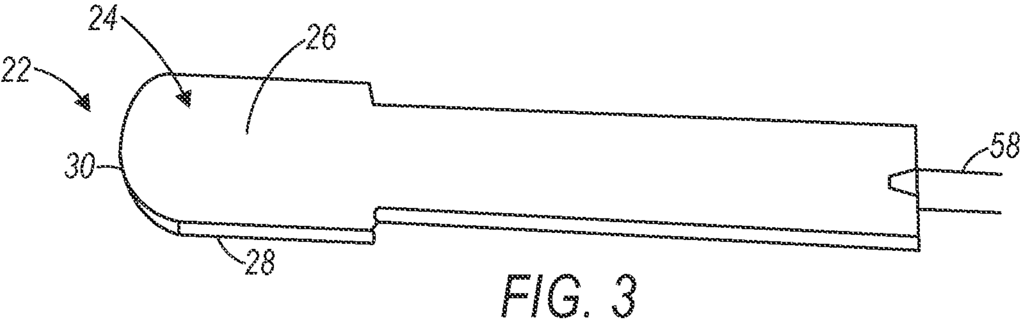
FIG. 3 illustrates a metal shim of a blade electrode.

FIG. 3 illustrates the metal shim 24 of a blade electrode 22. The metal shim 24 includes generally parallel and opposing metal shim faces 26. The metal shim faces 26 are connected by a metal shim facet 28. The metal shim 24 includes a distal end 30 opposite the handpiece 14 (not shown). Opposite the distal end 30, the metal shim 24 includes a first lead 58.

Figure 4:
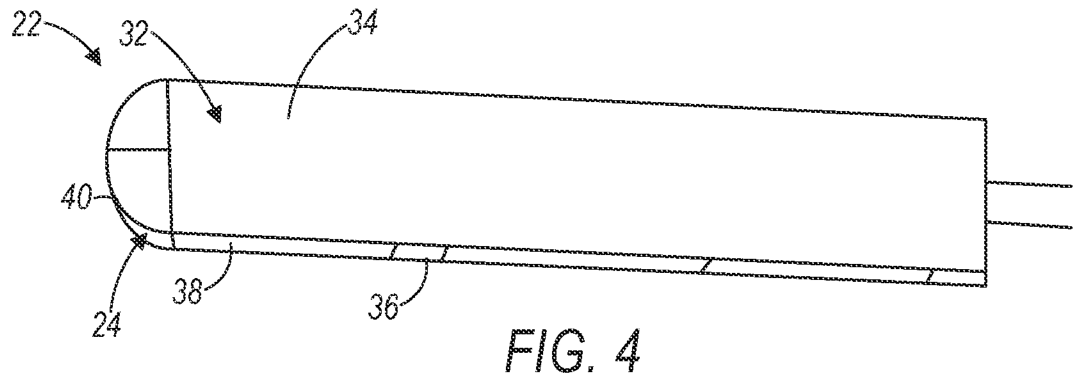
FIG. 4 illustrates a blade electrode.

FIG. 4 illustrates a blade electrode 22. The blade electrode includes a metal shim 24 partially covered with a nonconductive coating 32. The nonconductive coating 32 coats the metal shim faces 26 (not shown) to provide for coated metal shim faces 34. The nonconductive coating 32 coats part of the metal shim facet 28 (not shown) to provide for coated metal shim facet 36 and exposed metal shim facet 38. The exposed metal shim facet 38 includes the facet at the distal end 30 to provide for distal end exposed metal shim facet 40. The distal end exposed metal shim facet 40 may be referred to as the active region of the blade electrode 22.

Figure 5:
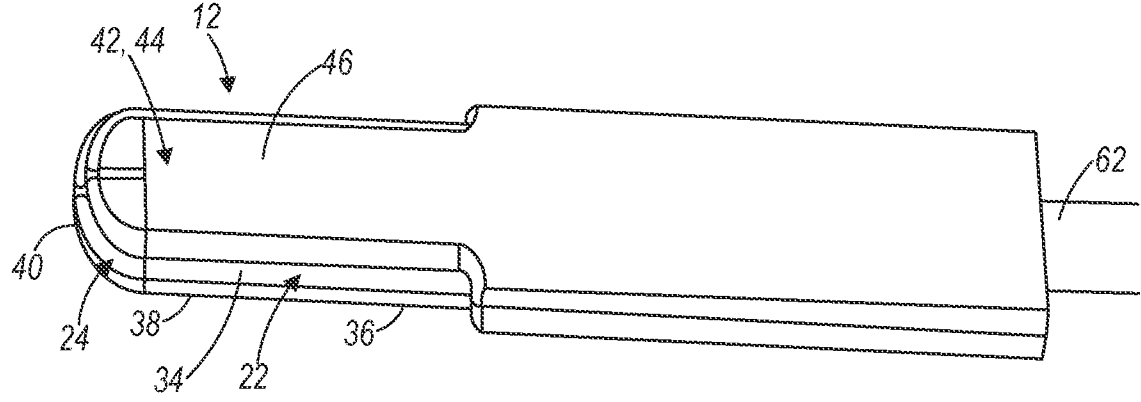
FIG. 5 illustrates a lateral electrode partially surrounding a blade electrode.

FIG. 5 illustrates a blade 12 of an electrosurgical device 10. The blade 12 includes a lateral electrode 42 located partially about the blade electrode 22. The lateral electrode 42 includes a broad shim 44. The broad shim 44 includes conductive faces 46. The conductive faces 46 face outwardly and are generally parallel to the coated metal shim faces 34. Opposing the conductive faces 46, the broad shim 44 includes interior faces 47 (not shown). The interior faces 47 are located parallel to the coated metal shim faces 34. Only part of the blade electrode 22 is in direct contact with the lateral electrode 42, so that at least part of the coated metal shim faces 34, coated metal shim facet 36, and exposed metal shim facet 38 protrude out of the lateral electrode 42. The lateral electrode 42 also includes a second lead 62 coaxial to the first lead 58 (not shown).

Figure 6:
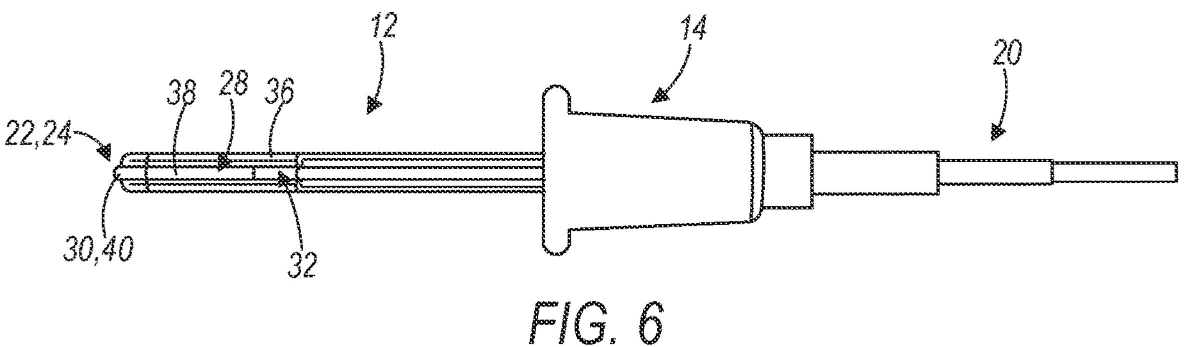
FIG. 6 illustrates a handpiece of an electrosurgical device.
Figure 7:
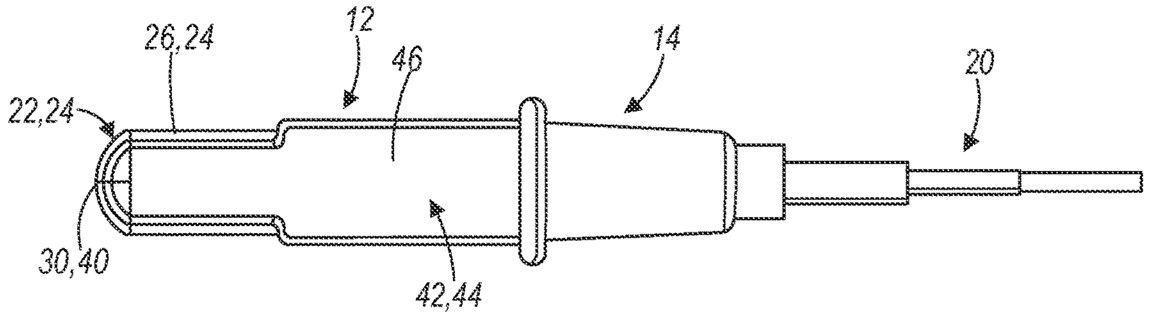
FIG. 7 illustrates a handpiece of an electrosurgical device.

FIGS. 6 and 7 illustrate a handpiece 14 and blade 12 of an electrosurgical device 10. The handpiece 14 is a handle for a user. The handpiece 14 is connected to a blade 12. The blade includes a blade electrode 22 partially surrounded by the lateral electrode 42. The lateral electrode 42 is stationary relative to the blade electrode 22. The lateral electrode 42 includes a broad shim 44. The broad shim 44 includes inside faces 47 (not shown) which are placed parallel to the coated metal shim faces 34. The nonconductive coating 32 insulates the blade electrode 22 from the lateral electrode 42.

Figures 8, 9, 10:
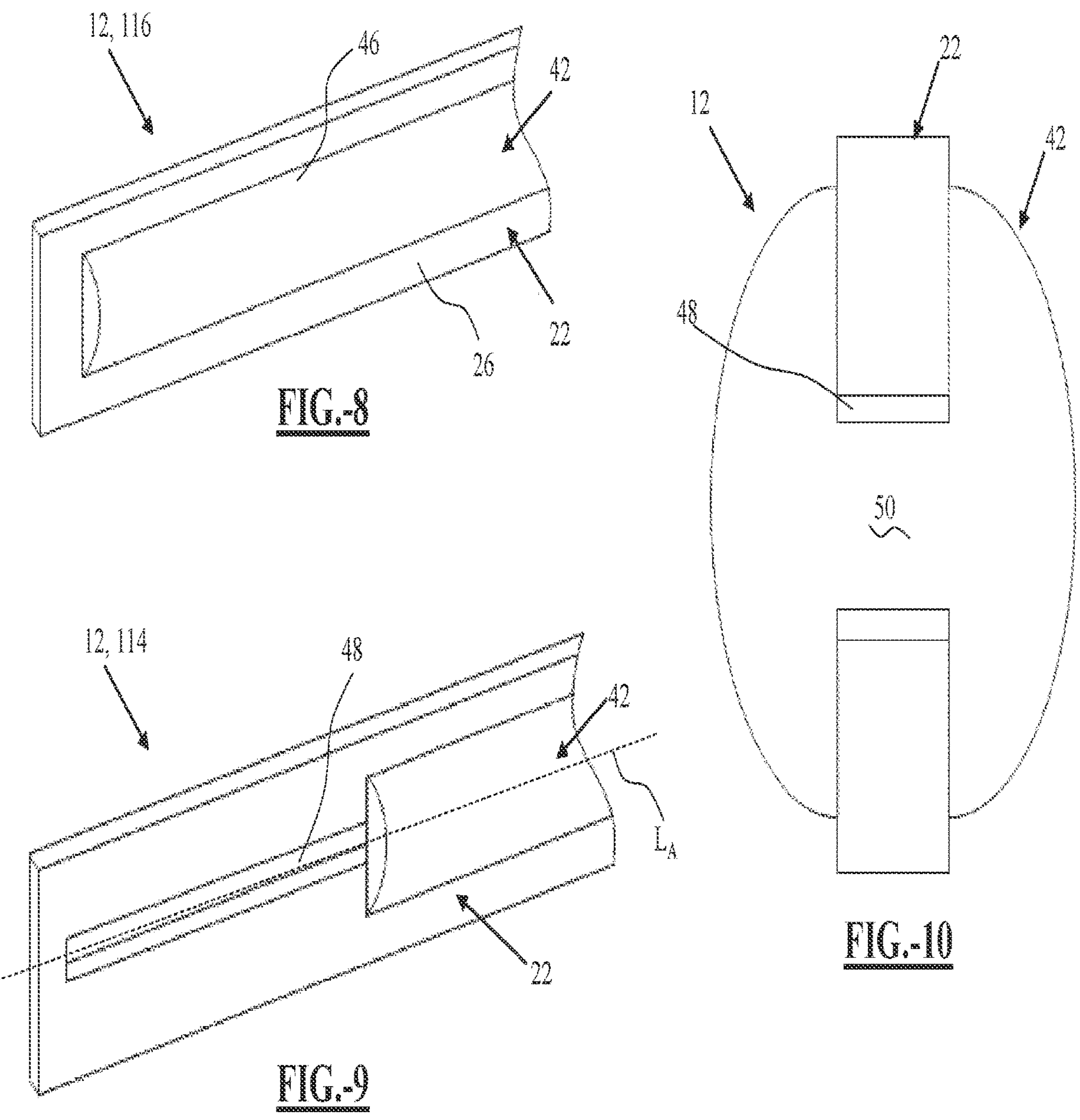
FIG. 8 illustrates a blade of an electrosurgical device in a retracted position.
FIG. 9 illustrates the blade of the electrosurgical device in an extended position.
FIG. 10 illustrates a cross-section of a blade of an electrosurgical device

FIG. 8 illustrates a blade 12 of an electrosurgical device 10. The blade 12 is in a retracted position 116. The retracted position 116 may be a physical configuration for a monopolar mode of the electrosurgical device 10. The retracted position 116 may be a physical configuration for a second monopolar mode (not shown) of the electrosurgical device 10. The blade 12 includes a blade electrode 22 and a lateral electrode 42. The lateral electrode 42 is placed parallel to the blade electrode 22. The lateral electrode 42 includes conductive faces 46 which face outwardly. The conductive faces 46 face opposite the faces 26 of the blade electrode 22.

FIG. 9 illustrates a blade 12 of an electrosurgical device 10. The blade 12 is in an extended position 114. The extended position 114 may be a physical configuration for a monopolar mode of the electrosurgical device 10. The extended position 114 may be a physical configuration for a first monopolar mode (not shown) of the electrosurgical device 10. The blade 12 includes a blade electrode 22. The blade electrode includes a receiving channel 48. The receiving channel 48 is engaged with an engagement portion 50 (as illustrated in FIG. 10) of a lateral electrode 42. The lateral electrode 42 is able to move along the length of the receiving channel 48. By moving along the length of the receiving channel 48, the lateral electrode 42 can move the blade 12 from the retracted position 116 to the extended position 114 and vice-versa.

FIG. 10 illustrates a cross-section of a blade 12 of an electrosurgical device 10. The blade includes a blade electrode 22 having a receiving channel 48. The receiving channel 48 receives an engagement portion 50 therein. The engagement portion 50 is part of the lateral electrode 42. The engagement portion 50 connects the two conductive faces 46 of the lateral electrode 50. The engagement portion 50 cooperates with the receiving channel 48 to allow the lateral electrode 42 to move from the extended position 114 to the retracted position 116 and vice-versa.

FIG. 11 illustrates a side view of a blade 12 of an electrosurgical device 10. The blade 12 is in a retracted position 116. The retracted position 116 may be a physical configuration for a monopolar mode of the electrosurgical device 10. The retracted position 116 may be a physical configuration for a second monopolar mode (not shown) of the electrosurgical device 10. The blade 12 includes a blade electrode 22. The blade electrode 22 is encircled or surrounded by a lateral electrode 42 when the blade electrode 22 is in the retracted position 116. In the retracted position 116, an active region 218 of the blade electrode 22 is flush with an active region of 220 of the lateral electrode 42. The active region 218 of the blade electrode 22 may include a metal shim facet 28 (not shown) and/or a metal shim face 26 (not shown) at a distal end 30. The blade electrode 22 may extend from the lateral electrode 42 into an extended position 114.

FIG. 12 illustrates a side view of a blade 12 of an electrosurgical device 10. The blade is in an extended position 114. The extended position 114 may be a physical configuration for a monopolar mode of the electrosurgical device 10. The extended position 114 may be a physical configuration for a first monopolar mode (not shown) of the electrosurgical device 10. The blade 12 includes a blade electrode 22. A portion of the blade electrode 22 is encircled or surrounded by a lateral electrode 42 when the blade electrode 22 is in the extended position 114. A portion of the blade electrode 22, including the active region 218, protrudes from the lateral electrode 42. In the extended position 114, an active region 218 of the blade electrode 22 is protrudes from an active region of 220 of the lateral electrode 42. The active region 218 of the blade electrode 22 may include a metal shim facet 28 and/or a metal shim face 26 at a distal end 30. The active region 218 may be coated with a conductive coating to provide for a conductive coated facet 222 and/or part of a conductive coated face 222 at a distal end 30 of the blade electrode. An exemplary conductive coating may include titanium nitride which may offer rapid heat transfer from the blade electrode distal end and prevent tissue sticking and charring. Adjacent to the conductive coated face 222, the blade electrode face may be coated with a nonconductive coating 32 (not shown) to provide for nonconductive coated faces 224. An exemplary nonconductive coating 32 (not shown) may include chromium nitride or a high velocity oxyfuel (HVOF) alumina spray which may serve as a non-stick coating, poor transmitter of electrical current, or both. The nonconductive coating 32 aid an electrical current to flow to the conductive coating, as the conductive coating offers a path of least resistance. The blade electrode 22 extends from an active region 220 of the lateral electrode 42. The active region 220 of the lateral electrode 42 includes both a conductive coating 226 and nonconductive coating 228. The conductive coating 226 may be located adjacent and/or about an opening 230 from which the blade electrode 22 protrudes from the lateral electrode 42. An exemplary conductive coating may include titanium nitride. A nonconductive coating 228 is located adjacent and/or about a perimeter of the conductive coating 226. Exemplary nonconductive coatings may include chromium nitride of HVOF alumina spray.

FIG. 12 further illustrates an exemplary control device (e.g., actuator) 232 of the electrosurgical device 10. The control device 232 includes a shuttle 234, a first button 236, and a second button 238. The shuttle 234 moves parallel to the longitudinal axis LA. Movement of the shuttle 234 results in movement of the blade electrode 22 along the longitudinal axis LA. Forward movement of the shuttle 234 (i.e., toward a distal end 30) results in the blade electrode 22 extending from the lateral electrode 42. Rearward movement of the shuttle 234 (i.e., away from a distal end 30) results in the blade electrode 22 retracting into the lateral electrode 42. The shuttle 234 exposes and/or covers one or more buttons, such as either the first button 236 or the second button 238. The first button 236 may be exposed when the blade electrode 22 is extended and covered when the blade electrode 22 is retracted. The second button 238 may be exposed when the blade electrode 22 is retracted and exposed when the blade electrode 22 is extended. The first button 236 when pressed may enable a first monopolar mode, first monopolar current, and/or first monopolar therapy signal. The second button 238 when pressed may enable a second monopolar mode, second monopolar current, and/or second monopolar therapy signal. The control device 232 may include or be in communication with one or more circuit switches 55 (not shown).

FIG. 13 illustrates a cross-section at A-A of the blade electrode 22. The blade electrode 22 may be formed of a plurality of materials. The blade electrode 22 may be formed as a sandwich composite. The blade electrode 22 includes a core material 240 and an outer material 242. An exemplary core material 240 may include copper. An exemplary outer material 242 may include stainless steel.

Figure 14:
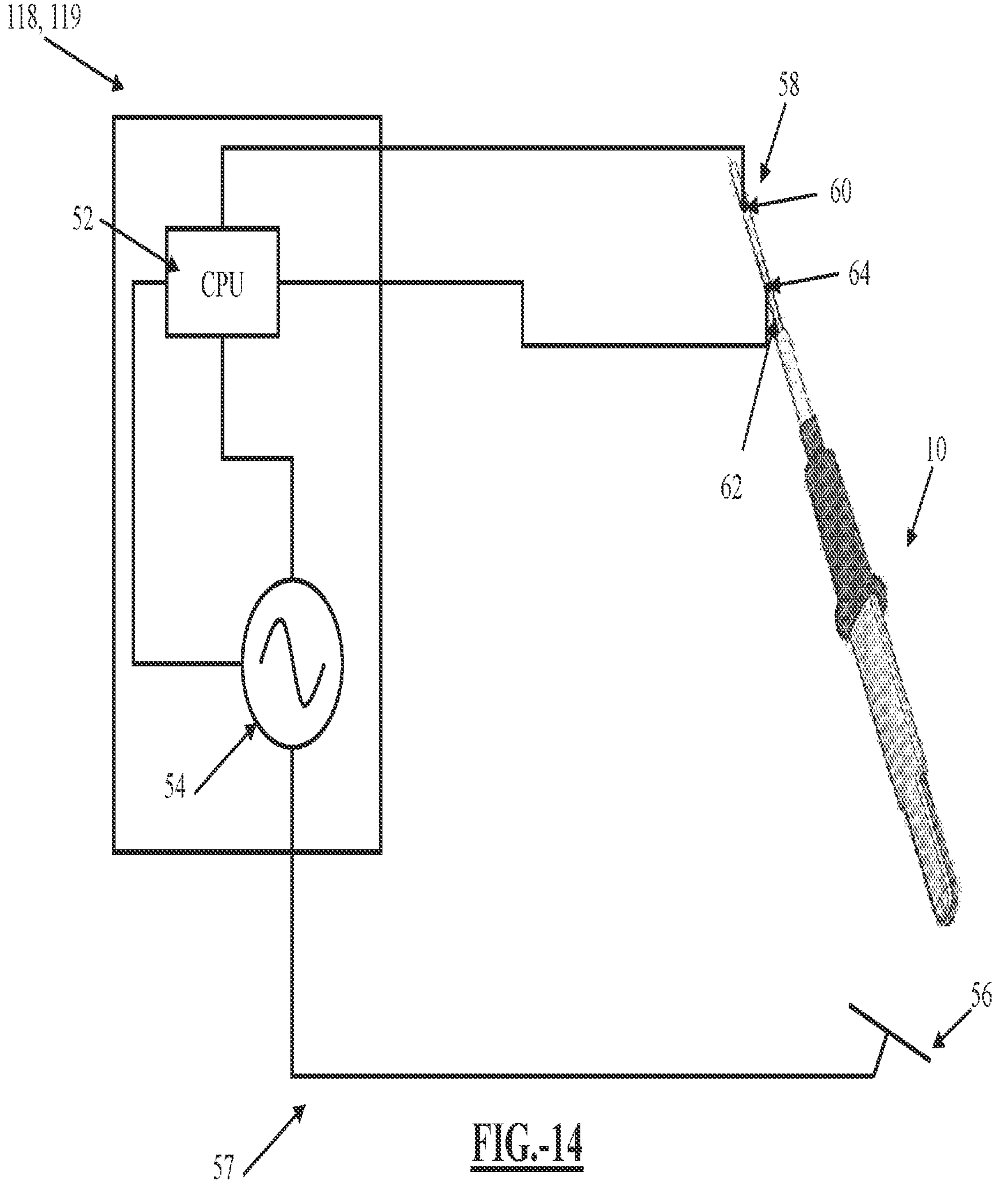
FIG. 14 illustrates a dual monopolar circuit of an electrosurgical system connected to the device according to the teachings.

FIG. 14 illustrates an exemplary electrosurgical system 118 and electrical circuit 119. The electrosurgical system 118 includes the electrosurgical device 10, a central processing unit 52, an energy source 54 (i.e., a generator), and a return electrode 56. The central processing unit 52 is electrically connected to the energy source 54. The central processing unit 52 is electrically connected to a first lead 58 and a second lead 62 of the electrosurgical device 10. The first lead 58 includes a first pole 60. The second lead 62 includes a second pole 64. The energy source 54 is electrically connected to a return electrode 56, forming a return path 57. The energy source 54 is in electrical communication with the first pole 60 and the second pole 64 through the central processing unit 52. A first monopolar mode may provide for a first monopolar therapy current which travels from the energy source 54 to the central processing unit 52, from the central processing unit 52 to the first pole 60, from the first pole 60 to the return electrode 56 (such as through tissue between the first pole 60 and the return electrode 56), from the return electrode 56 through the return path 57 back to the energy source 54. A second monopolar mode may include the first monopolar therapy current and an additional second monopolar therapy current, or only a second therapy current. The second monopolar therapy current may travel from the energy source 54 to the central processing unit 52, from the central processing unit 52 to the second pole 64, from the second pole 64 to the return electrode 56 (such as through tissue between the second pole 64 and the return electrode 56), from the return electrode 56 through the return path 57 back to the energy source 54.

Figures 15, 16, 17:
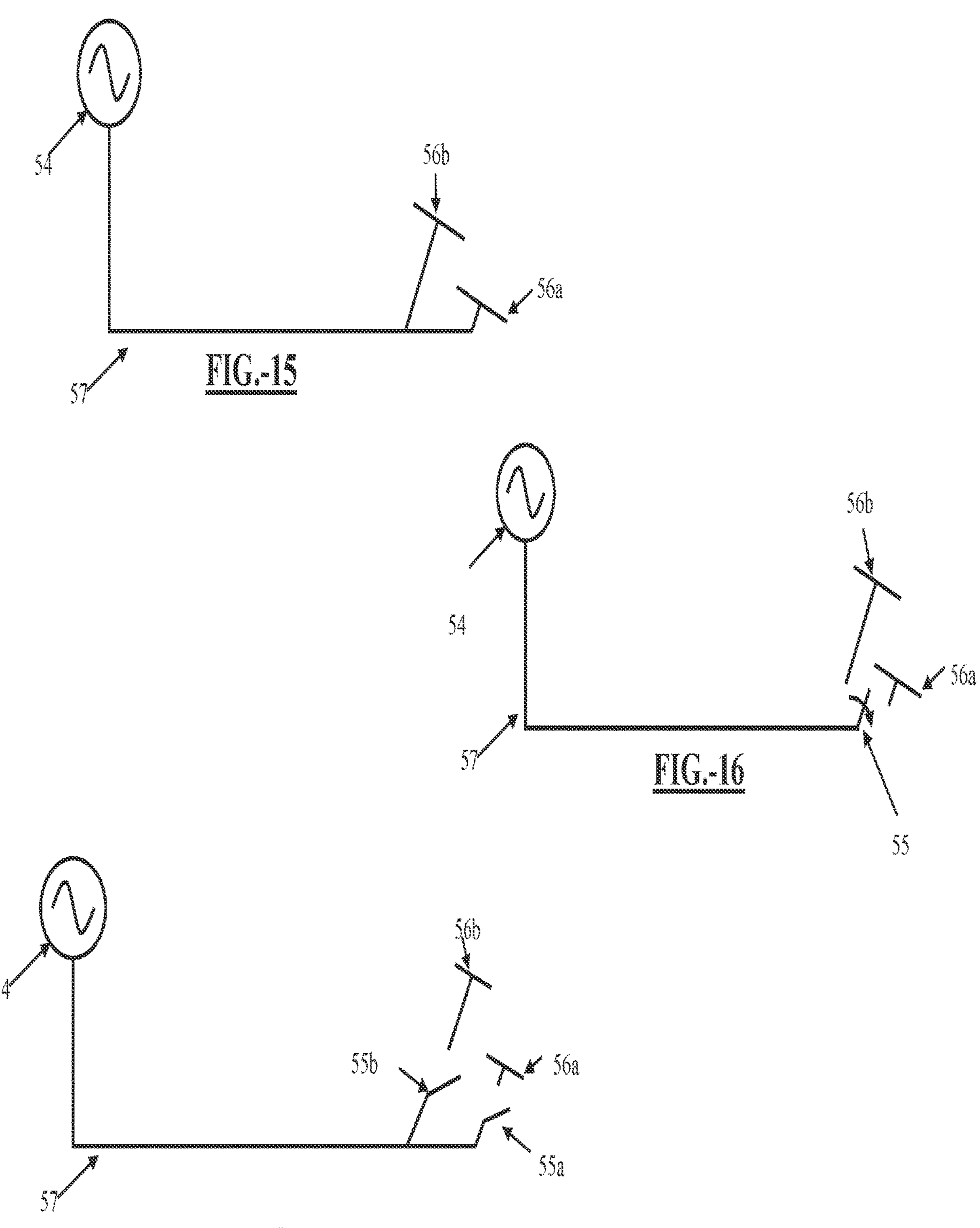
FIG. 15 illustrates a portion of a circuit of an electrosurgical system having multiple return electrodes.
FIG. 16 illustrates a portion of a circuit including multiple return electrodes including a switch between the return electrodes.
FIG. 17 illustrates a partial circuit including a return path with two switches.

FIGS. 15, 16, and 17 illustrate exemplary return electrode(s) 56 and return paths 57. The return electrode 56 may include a single return electrode 56, as shown in FIG. 14. A single electrode 56 allows the first pole 60 (i.e., blade electrode) (not shown) and the second pole 64 (i.e., lateral electrode) (not shown) to share a common return electrode 56. The return electrode 56 may include a plurality of return electrodes, such as a first return electrode **56*a* and a second return electrode 56*b*. The first pole 60 and the second pole 64 may have individual return electrodes 56. The first pole 60 may be in electrical communication with a first return electrode 56*a*. The second pole 64 may be in electrical communication with a second return electrode 56*b*. The return path 57 may be in direct and constant electrical communication with the return electrode 56, first return electrode 56*a*, and/or second return electrode 56*b*. The return path 57 may include one or more electrical switches 55 to control electrical communication with the return electrode 56, first electrode 56*a*, and/or second electrode 56*b*. The one or more electrical switches 55 may include a single switch 55 which switches between a first return electrode 56*a* and a second return electrode 56*b*. The one or more electrical switches 55 may include a first electrical switch 55*a* and a second electrical switch 55*b*. A first electrical switch 55*a* may open or close the electrical return path 57 from the first return electrode 56*a* to the energy source 54. A second electrical switch 55*b* may open or close the electrical return pat 57 from the second return electrode 56*b* to the energy source 54**.

Figure 18A:
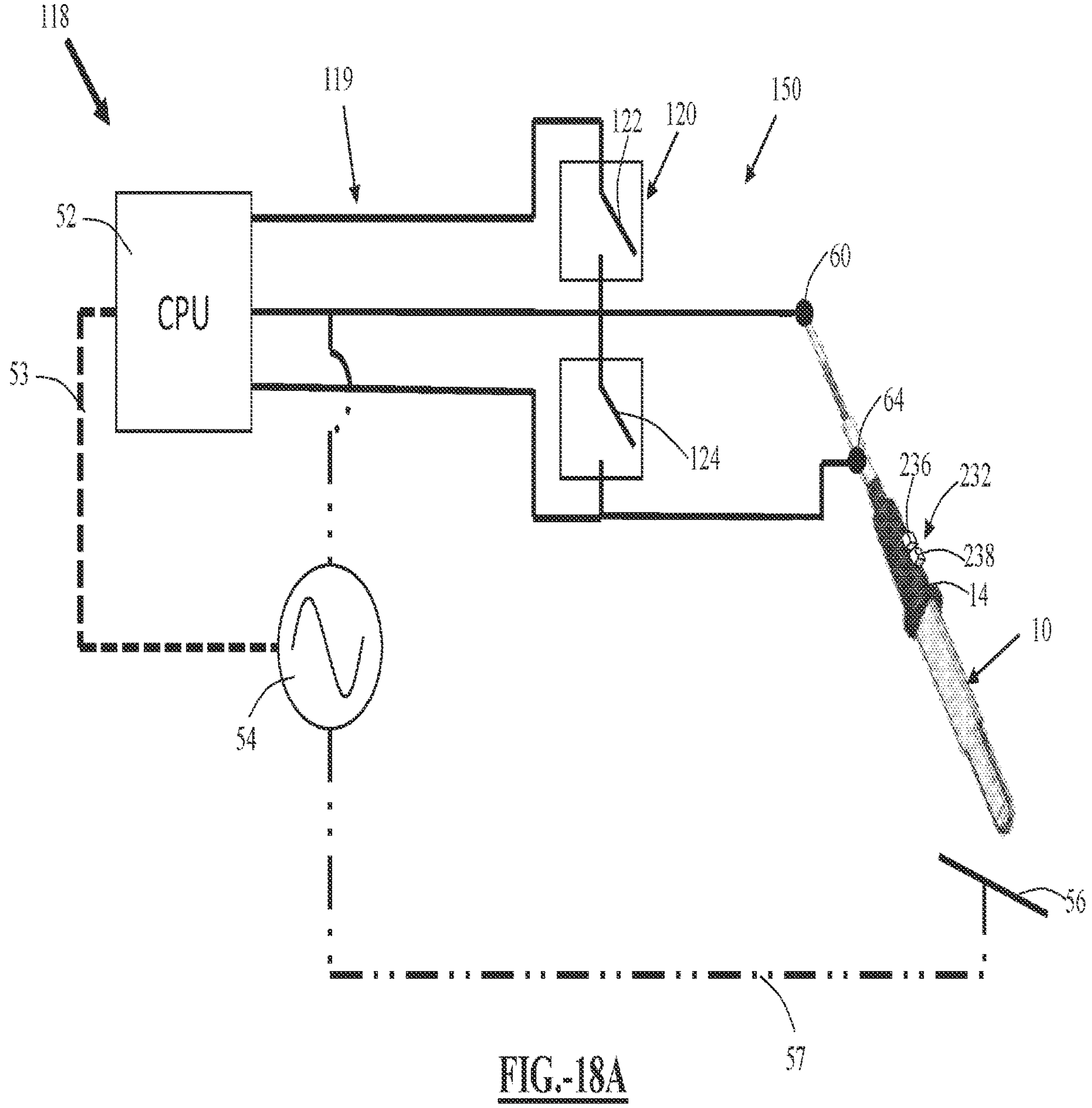
FIG. 18A illustrates an electrical circuit of a dual monopolar circuit in a non-electrosurgical mode.

FIG. 18A illustrates an electrical circuit 119 with the electrosurgical device 10 integrated into an electrosurgical system 118. FIG. 18A illustrates the electrical circuit 119 in a powered off or non-electrosurgical mode. The electrical circuit 119 includes a central processing unit 52 connected to and in communication with an energy source 54 via a communication line 53. The energy source is in communication with a return electrode 56 via a return path 57. The electrical circuit 119 includes a plurality of switches 120 which are part of or in electrical communication with a control device 232. The electrosurgical system 118 includes a control device 232. The control device 232 is part of the electrosurgical device 10 and is located on the handpiece 14. The control device 232 includes one or more buttons 236, 238 in electrical communication with one or more switches 120. The one or more switches include a first monopolar mode switch 122 and a second monopolar mode switch 124. When the one or more switches 120 are open, the electrosurgical device 10 is powered off and/or in a non-electrosurgical mode. Specifically, when the first switch 122 and the second switch 124 are both open, the electrosurgical device 10 is powered off and/or in a non-electrosurgical mode 150 such that the first pole 60 and the second pole 64 do not receive electrical power, signal, and/or current. The first switch 122 and the second switch 124 are open when the first button 236 and the second button 238 are both unpressed.

Figure 18B:
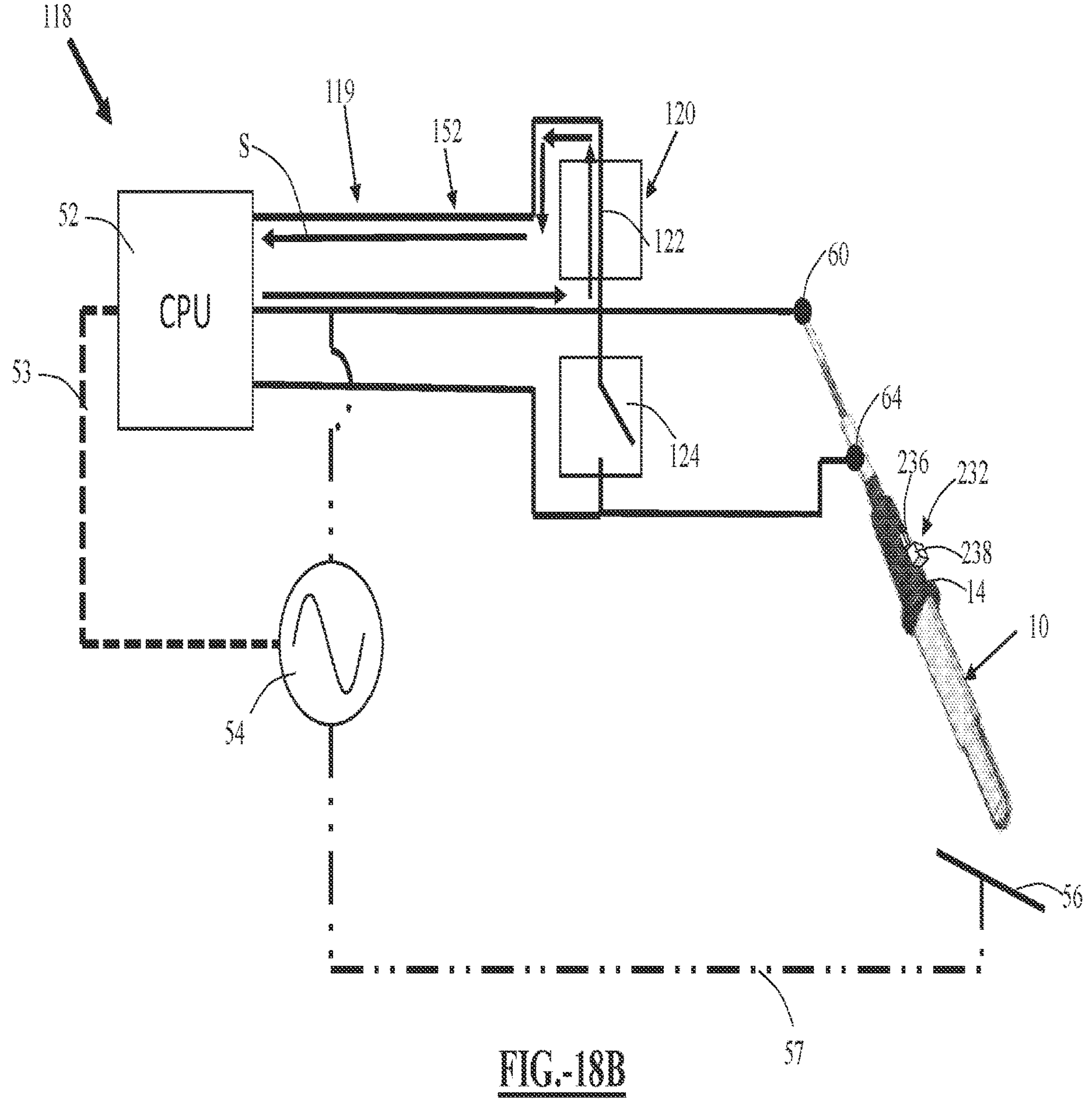
FIG. 18B illustrates an electrical circuit of a dual monopolar circuit in a first monopolar mode.
Figure 18C:
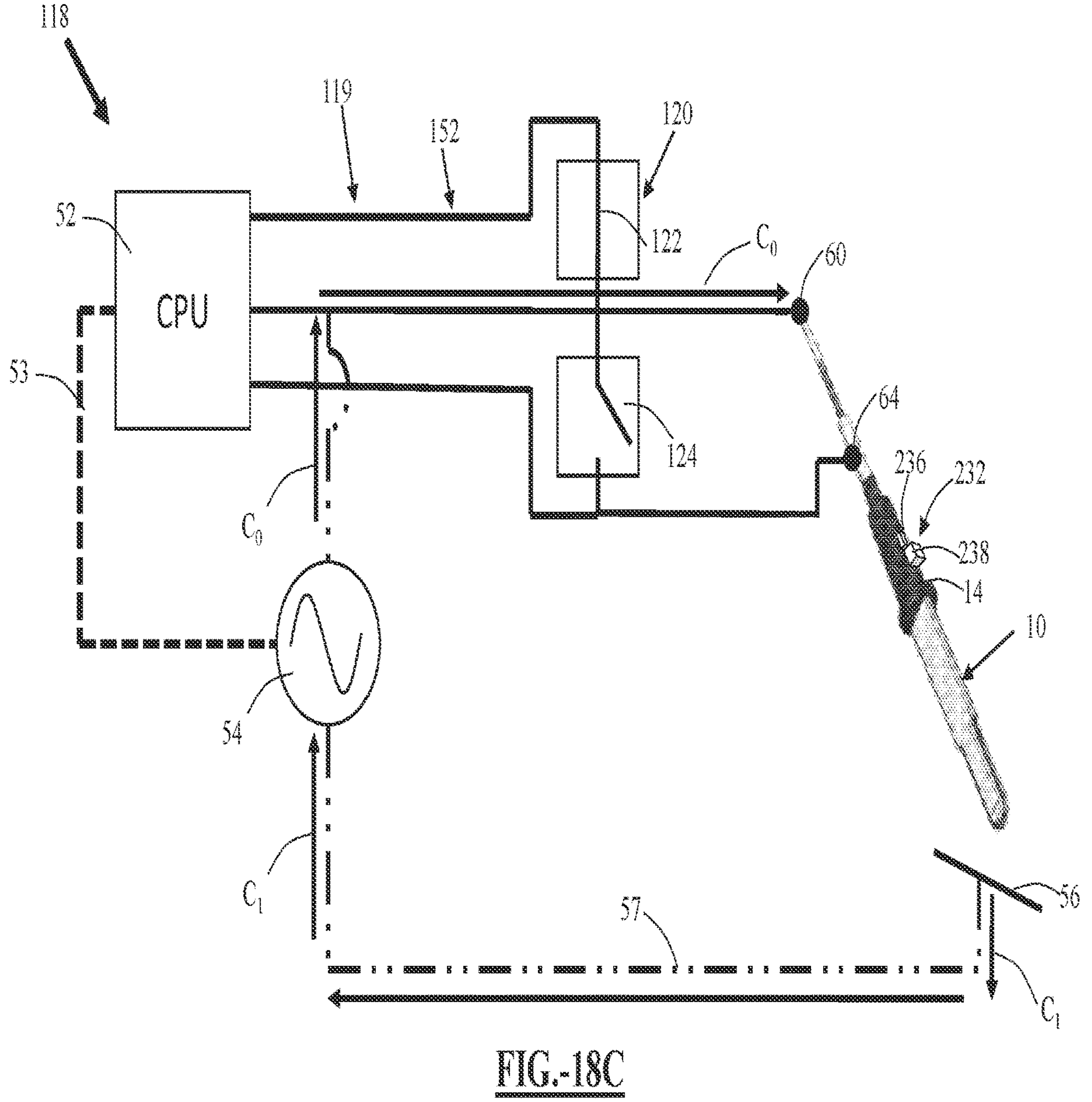
FIG. 18C illustrates an electrical circuit of a dual monopolar circuit in a first monopolar mode.

FIGS. 18B and 18C illustrate an electrical circuit 119 of an electrosurgical system 118 in a first monopolar mode or forming a first signaling circuit 152. In the first monopolar mode 152 a first button 236 is pressed, such as by a user (i.e., surgeon). The first button 236 is directly connected to or in electrical communication with a first switch 122. Pressing of the first button 236 results in the first switch 122 closing to form a first signaling circuit 152. The central processing unit 52 monitors for continuity of a signal S passing through the first switch 122 when closed, such that the signal S flows from the central processing unit 52, through the first switch 122, and returns to the central processing unit 52 (as shown in FIG. 18B) When the first switch 122 is closed, continuity is formed between the first switch 122 and the central processing unit 52.

When the central processing unit 52 senses the first switch 122 is closed, the central processing unit 52 sends instructions via the communication line 53 to the energy source 54 to provide a therapy current $C_0$. As shown in FIG. 18C, the therapy current $C_0$ is delivered from the energy source 54 to the first pole 60. As the second switch 124 is open, the therapy current $C_0$ from the energy source 54 is prevented from being delivered to the second pole 64. The first pole 60 transfers the therapy current $C_0$ as a first therapy current $C_1$ to the return electrode 56. The first therapy current $C_1$ is then delivered from the return electrode 56 to the energy source 54.

Figure 18D:
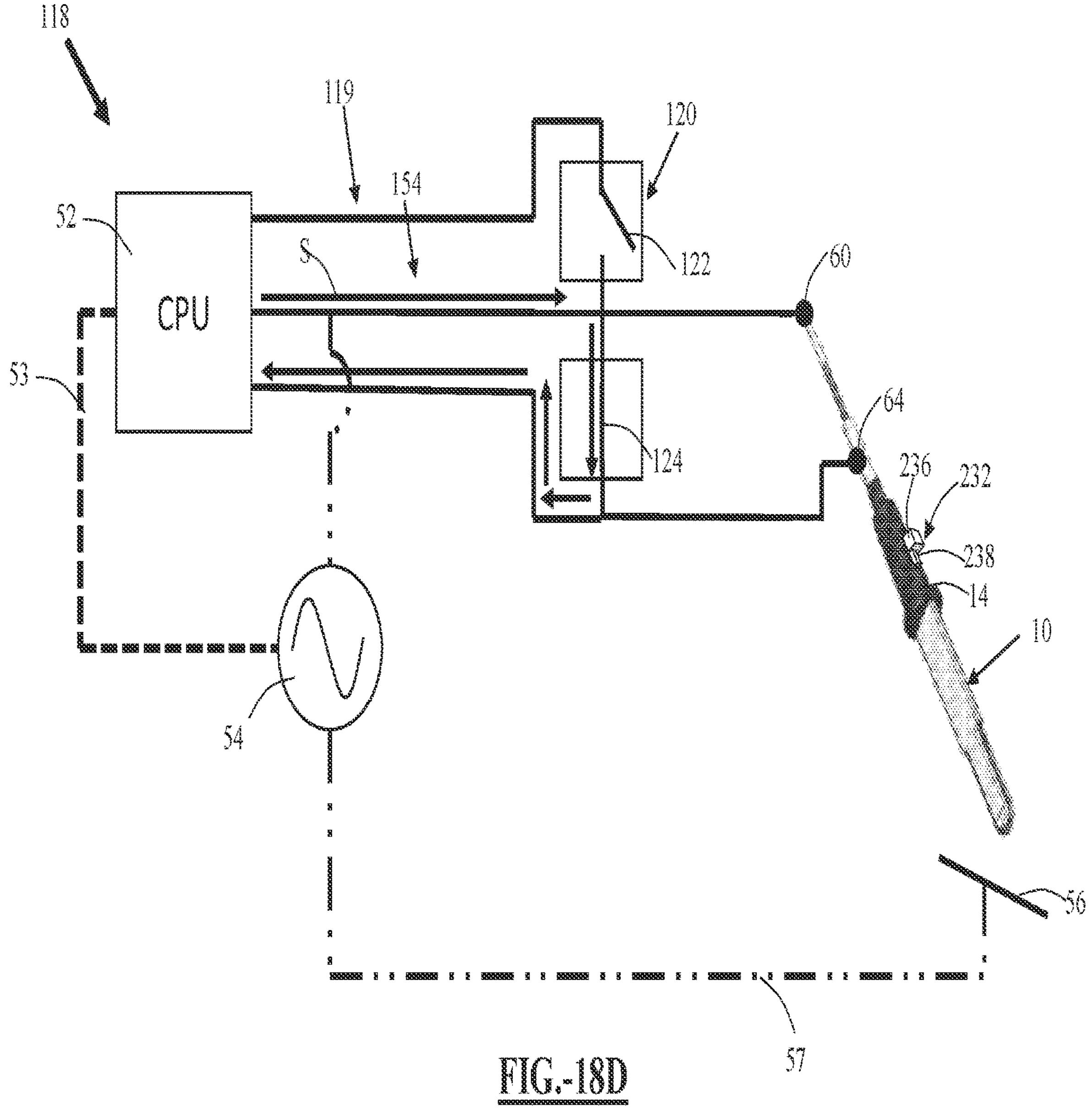
FIG. 18D illustrates an electrical circuit of a dual monopolar circuit in a second monopolar mode.
Figure 18E:
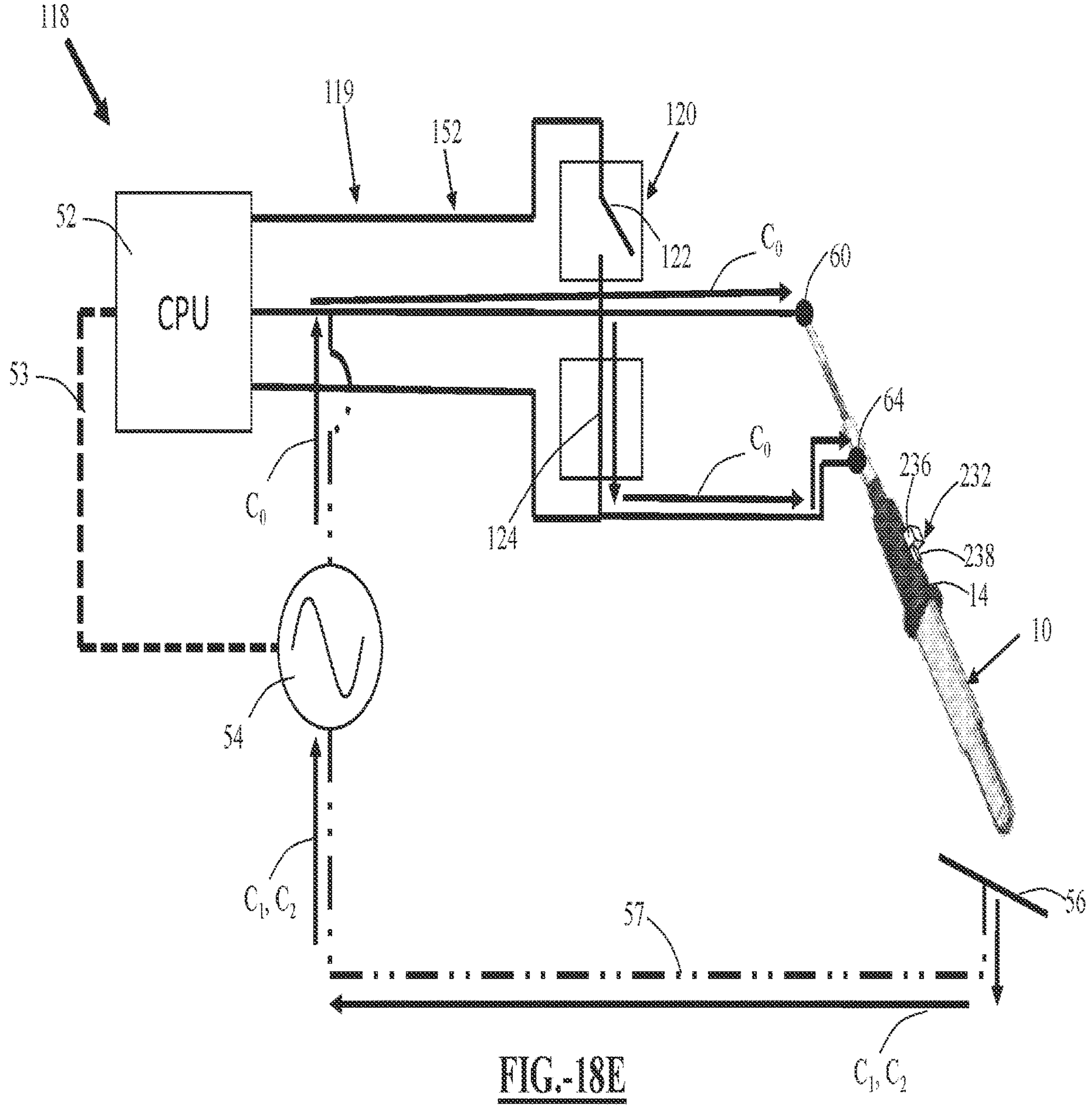
FIG. 18E illustrates an electrical circuit of a dual monopolar circuit in a second monopolar mode.

FIGS. 18D and 18E illustrate an electrical circuit 119 of an electrosurgical system 118 in a second monopolar mode or forming a second signaling circuit 154. In the second monopolar mode 154 a second button is pressed by a user (i.e., surgeon). The second button 238 is either directly connected to or in electrical communication with a second switch 124. Pressing of the second button 238 results in the second switch 124 closing to form the second signaling circuit 154. The central processing unit 52 monitors for continuity of a signal S passing through the second switch 124 when closed, such that the signal S flows from the central processing unit 52, through the second switch 124 when closed, and returns to the central processing unit 52 (as shown in FIG. 18C). When the second switch 124 is closed, continuity is formed between the second switch 124 and the central processing unit 52.

When the central processing unit 52 senses the second switch 124 is closed, the central processing unit 52 sends instructions to the energy source 54 to provide a therapy current $C_0$. As shown in FIG. 18E, the therapy current $C_0$ is delivered from the energy source 54 to both the first pole 60 and the second pole 64. As the second switch 124 is closed, the therapy current $C_0$ from the energy source 54 travels to both the first pole 60 and also through the second switch 124 to the second pole 64. The first pole 60 transfers the therapy current $C_0$ as a first therapy current $C_1$ to the return electrode 56. The second pole 64 transfers the therapy current $C_0$ as a second therapy current $C_2$ to the return electrode 56. Both the first therapy current $C_1$ and the second therapy current $C_2$ are then delivered from the return electrode 56 to the energy source 54.

Unless otherwise stated, any numerical values recited herein include all values from the lower value to the upper value in increments of one unit provided that there is a separation of at least 2 units between any lower value and any higher value. As an example, if it is stated that the amount of a component, a property, or a value of a process variable such as, for example, temperature, pressure, time and the like is, for example, from 1 to 90, preferably from 20 to 80, more preferably from 30 to 70, it is intended that intermediate range values such as (for example, 15 to 85, 22 to 68, 43 to 51, 30 to 32 etc.) are within the teachings of this specification. Likewise, individual intermediate values are also within the present teachings. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of, or even consist of the elements, ingredients, components or steps. Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

The invention claimed is:

1. An electrosurgical device comprising:

a first pole;

a second pole;

a blade electrode configured to perform a cutting operation in a first monopolar mode, the blade electrode having:

a first shim having:

two faces which are generally opposing; and one or more facets connecting the two faces;

a nonconductive coating which covers at least one of the two faces and at least a portion of the one or more facets of the first shim; and a receiving channel;

a lateral electrode including a second shim having one or more conductive faces, the lateral electrode having an engagement portion configured to engage with the receiving channel, the lateral electrode configured to perform a coagulation operation in a second monopolar mode, wherein:

the second shim is located parallel to the blade electrode so that at least one of the one or more conductive faces is exposed;

a distal end of the blade electrode protrudes from the lateral electrode;

the first pole is connected to the blade electrode via a first lead and the second pole is connected to the lateral electrode via a second lead;

the first lead is coaxial with the second lead and an insulator is disposed between the first lead and the second lead;

the electrosurgical device is able to operate in the first monopolar mode and the second monopolar mode; and the electrosurgical device is configured to transmit a first therapy signal corresponding to the cutting operation in the second monopolar mode from the first pole concurrently with a second therapy signal corresponding with the coagulation operation in the second monopolar mode from the second pole.

2. The electrosurgical device of claim 1, wherein the first shim includes a first side and the portion covered by the nonconductive coating is on the first side and an additional portion of the first shim at the first side remains exposed relative to the nonconductive coating.

3. The electrosurgical device of claim 2, wherein the first shim includes a second side that is covered with the nonconductive coating.

4. The electrosurgical device of claim 1, the electrosurgical device further comprising a first monopolar mode switch and a second monopolar mode switch wherein:

when the first monopolar mode switch is closed and the second monopolar mode switch is open, the electrosurgical device operates in the first monopolar mode and the second pole is not utilized; and when the first monopolar mode switch is open and the second monopolar mode switch is closed, the electrosurgical device operates in the second monopolar mode and both the first pole and the second pole are utilized.

5. The electrosurgical device of claim 1, wherein the electrosurgical device is part of an electrosurgical system having a single return electrode in communication with an energy source via a return path and 20% to 90% of a surface area of the nonconductive coating of the blade electrode is in direct contact with the lateral electrode.

6. The electrosurgical device of claim 5, wherein;

the blade electrode and the lateral electrode are in electrical communication with the energy source;

when in the first monopolar mode, an electrical signal from the energy source is received by the blade electrode and not received by the lateral electrode and then the electrical signal is transferred to the single return electrode; and when in the second monopolar mode, the electrical signal from the energy source is received by both the blade electrode and the lateral electrode and then the electrical signal is transferred to the single return electrode.

7. The electrosurgical device of claim 1, wherein:

the electrosurgical device is part of an electrosurgical system having a single return electrode in communication with an energy source via a return path; and both the blade electrode and the lateral electrode are in electrical communication with the single return electrode.

8. The electrosurgical device of claim 1, wherein;

the electrosurgical device is part of an electrosurgical system having first and second monopolar mode switches that are positioned between an energy source and the lateral electrode;

the second monopolar mode switch is open in the first monopolar mode so that an electrical signal from the energy source is prevented from being delivered to the lateral electrode; and the second monopolar mode switch is closed in the second monopolar mode so that the electrical signal from the energy source is delivered to the lateral electrode.

9. An electrosurgical device comprising:

a first pole;

a second pole;

a blade electrode configured to perform a cutting operation in a first monopolar mode, the blade electrode having:

a first shim having:

two faces which are generally opposing; and one or more facets connecting the two faces;

a nonconductive coating which covers at least one of the two faces and at least a portion of the one or more facets of the first shim; and a receiving channel;

a lateral electrode having a second shim that includes one or more conductive faces, the lateral electrode having an engagement portion configured to engage with the receiving channel, the lateral electrode configured to perform a coagulation operation in a second monopolar mode, wherein:

the second shim is a conductive tube which at least partially encircles the blade electrode, so that at least one of the one or more conductive faces is exposed and a distal end of the blade electrode protrudes from the lateral electrode, wherein:

the nonconductive coating insulates the blade electrode from the lateral electrode;

the first pole is connected to the blade electrode via a first lead and the second pole is connected to the lateral electrode via a second lead;

the first lead is coaxial with the second lead and an insulator is disposed between the first lead and the second lead;

the electrosurgical device is able to operate in the first monopolar mode and the second monopolar mode; and the electrosurgical device is configured to transmit a first therapy signal corresponding to the cutting operation in the second monopolar mode from the first pole concurrently with a second therapy signal corresponding with the coagulation operation in the second monopolar mode from the second pole.

10. The electrosurgical device of claim 9, wherein the first shim includes a first side and the portion covered by the nonconductive coating is on the first side and an additional portion of the first shim at the first side remains exposed relative to the nonconductive coating.

11. The electrosurgical device of claim 10, wherein the first shim includes a second side that is covered with the nonconductive coating.

12. The electrosurgical device of claim 9, the electrosurgical device further comprising a first monopolar mode switch and a second monopolar mode switch, wherein:

when the first monopolar mode switch is closed and the second monopolar mode is open, the electrosurgical device operates in the first monopolar mode and the second pole is not utilized; and when the first monopolar mode switch is open and the second monopolar mode is closed, the electrosurgical device operates in the second monopolar mode and both the first pole and the second pole are utilized.

13. An electrosurgical device comprising:

a first pole;

a second pole;

a blade electrode configured to perform a cutting operation in a first monopolar mode, the blade electrode having:

a first shim having:

two faces which are generally opposing; and one or more facets connecting the two faces;

a nonconductive coating which covers at least one of the two faces and at least a portion of the one or more facets of the first shim, wherein the first shim includes a first side and a second side and the portion covered by the nonconductive coating is on the first side and an additional portion of the first shim at the first side remains exposed relative to the nonconductive coating, wherein the second side is covered with the nonconductive coating; and a receiving channel;

a lateral electrode including a second shim having one or more conductive faces, the lateral electrode having an engagement portion configured to engage with the receiving channel the lateral electrode configured to perform a coagulation operation in a second monopolar mode, wherein:

the second shim is located parallel to the blade electrode so that at least one of the one or more conductive faces is exposed;

a distal end of the blade electrode protrudes from the lateral electrode;

the first pole is connected to the blade electrode via a first lead and the second pole is connected to the lateral electrode via a second lead;

the first lead is coaxial with the second lead and an insulator is disposed between the first lead and the second lead;

the electrosurgical device is able to operate in the first monopolar mode and the second monopolar mode; and the electrosurgical device is configured to transmit a first therapy signal corresponding to the cutting operation in the second monopolar mode from the first pole concurrently with a second therapy signal corresponding with the coagulation operation in the second monopolar mode from the second pole.

14. The electrosurgical device of claim 13, the electrosurgical device further comprising a first monopolar mode switch and a second monopolar mode switch, wherein:

when the first monopolar mode switch is closed and the second monopolar mode switch is open, the electrosurgical device operates in the first monopolar mode and the second pole is not utilized; and when the first monopolar mode switch is open and the second monopolar mode switch is closed, the electrosurgical device operates in the second monopolar mode and both the first pole and the second pole are utilized.

15. The electrosurgical device of claim 13, wherein the electrosurgical device is part of an electrosurgical system having a single return electrode in communication with an energy source via a return path and 20% to 90% of a surface area of the nonconductive coating of the blade electrode is in direct contact with the lateral electrode.

16. The electrosurgical device of claim 15, wherein:

the blade electrode and the lateral electrode are in electrical communication with the energy source;

when in the first monopolar mode, an electrical signal from the energy source is received by the blade electrode and not received by the lateral electrode and then the electrical signal is transferred to the single return electrode; and when in the second monopolar mode, the electrical signal from the energy source is received by both the blade electrode and the lateral electrode and then the electrical signal is transferred to the single return electrode.

17. The electrosurgical device of claim 13, wherein;

the electrosurgical device is part of an electrosurgical system having a single return electrode in communication with an energy source via a return path; and both the blade electrode and the lateral electrode are in electrical communication with the single return electrode.

18. The electrosurgical device of claim 13, wherein:

the electrosurgical device is part of an electrosurgical system having first and second monopolar mode switches that are positioned between an energy source and the lateral electrode;

the second monopolar mode switch is open in the first monopolar mode so that an electrical signal from the energy source is prevented from being delivered to the lateral electrode; and the second monopolar mode switch is closed in the second monopolar mode so that the electrical signal from the energy source is delivered to the lateral electrode.

* * * * *